(12) United States Patent
Argyropoulos

(10) Patent No.: US 7,959,765 B2
(45) Date of Patent: Jun. 14, 2011

(54) PRODUCT PREPARATION AND RECOVERY FROM THERMOLYSIS OF LIGNOCELLULOSICS IN IONIC LIQUIDS

(75) Inventor: Dimitris Argyropoulos, Raleigh, NC (US)

(73) Assignee: North Carolina State Universtiy, Raleigh, NC (US)

( * ) Notice: Subject to any disclaimer, the term of this patent is extended or adjusted under 35 U.S.C. 154(b) by 446 days.

(21) Appl. No.: 12/026,993

(22) Filed: Feb. 6, 2008

(65) Prior Publication Data
US 2008/0185112 A1 Aug. 7, 2008

Related U.S. Application Data

(60) Provisional application No. 60/888,453, filed on Feb. 6, 2007.

(51) Int. Cl.
*C10B 49/00* (2006.01)
*C10G 1/00* (2006.01)
(52) U.S. Cl. ............. 201/2.5; 201/30; 201/40; 585/240; 585/242
(58) Field of Classification Search .................. 201/2.5, 201/30, 41; 585/240, 242; 162/9, 50, 91–98, 162/189
See application file for complete search history.

(56) References Cited

U.S. PATENT DOCUMENTS

| | | | |
|---|---|---|---|
| 1,924,238 A | 8/1933 | Graenacher | |
| 1,943,176 A | 1/1934 | Graenacher | |
| 3,926,947 A | 12/1975 | Lipska | |
| 4,752,579 A | 6/1988 | Arena et al. | |
| 5,221,537 A | 6/1993 | Hecht et al. | |
| 5,395,455 A * | 3/1995 | Scott et al. | 127/37 |
| 5,536,325 A | 7/1996 | Brink | |
| 5,628,830 A | 5/1997 | Brink | |
| 5,892,107 A * | 4/1999 | Farone et al. | 562/515 |
| 5,916,780 A | 6/1999 | Foody et al. | |
| 6,509,180 B1 | 1/2003 | Verser et al. | |
| 6,824,559 B2 | 11/2004 | Michal | |
| 6,824,599 B2 * | 11/2004 | Swatloski et al. | 106/163.01 |
| 6,855,180 B1 * | 2/2005 | Pinatti et al. | 44/307 |
| 7,109,005 B2 | 9/2006 | Eroma et al. | |
| 7,157,588 B2 * | 1/2007 | Harmer et al. | 548/543 |
| 7,309,602 B2 | 12/2007 | David | |
| 2007/0161095 A1 * | 7/2007 | Gurin | 435/134 |
| 2008/0023162 A1 * | 1/2008 | Myllymaki et al. | 162/163 |
| 2008/0307703 A1 * | 12/2008 | Dietenberger et al. | 48/76 |

FOREIGN PATENT DOCUMENTS

| | | |
|---|---|---|
| DE | 10 2005 017 715 A1 | 10/2006 |
| DE | 10 2005 017 733 A1 | 10/2006 |
| EP | 1 860 201 | 11/2007 |
| WO | WO 03/029329 | 4/2003 |
| WO | WO 2005/017001 A1 | 2/2005 |

(Continued)

OTHER PUBLICATIONS

Abstract "Novozymes Working With Chinese on Ethanol From Cellulose," *Focus on Catalysts*, 2006, p. 4, vol. 2006, No. 8.

(Continued)

*Primary Examiner* — N. Bhat
(74) *Attorney, Agent, or Firm* — Alston & Bird LLP

(57) ABSTRACT

Methods for the thermolysis of lignocellulosic materials, such as wood, cellulose, lignin, and lignocellulose are provided. Some methods comprise combining the lignocellulosic material with an ionic liquid and subjecting the mixture of the lignocellulosic material and the ionic media to thermolysis conditions to form a recoverable product, such as a commodity chemical.

30 Claims, 3 Drawing Sheets

FOREIGN PATENT DOCUMENTS

| WO | WO 2005/017252 |  | 2/2005 |
| --- | --- | --- | --- |
| WO | WO 2005/023873 | A1 | 3/2005 |
| WO | WO 2005/054298 | A1 | 6/2005 |
| WO | WO 2005/066374 | A1 | 7/2005 |
| WO | WO 2005/098546 | A2 | 10/2005 |
| WO | WO 2006/265544 |  | 10/2006 |
| WO | WO 2007/005388 |  | 1/2007 |
| WO | WO 2007/112382 |  | 10/2007 |
| WO | WO 2007/128268 |  | 11/2007 |
| WO | WO 2007/144282 |  | 12/2007 |
| WO | WO 2007/147813 |  | 12/2007 |
| WO | WO 2008/000666 |  | 1/2008 |
| WO | WO 2008/003643 |  | 1/2008 |
| WO | WO 2008/019219 | A1 | 2/2008 |
| WO | WO 2008/045021 |  | 4/2008 |

OTHER PUBLICATIONS

Alcañiz-Monge et al., "Development of New Carbon Honeycomb Structures From Cellulose and Pitch," *Carbon*, 2002, pp. 541-550, vol. 40.

Grethlein, "Chemical Breakdown of Cellulosic Materials," *Journal of Applied Chemistry and Biotechnology*, 1978, pp. 296-308, vol. 28, No. 4.

Hang et al., "Enzymatic Production of Soluble Sugars From Corn Husks," *Lebensmittal-Wissenschaft Und Technologie*, 1999, pp. 208-210, vol. 32, No. 4.

Kadla et al., "Lignin-Based Caron Fibers for Composite Fiber Applications," *Carbon*, 2002, pp. 2913-2920, vol. 40.

Katz et al., "Production of Glucose by Enzymatic Hydrolysis of Cellulose," *Applied Microbiology*, 1968, pp. 419-420, vol. 16, 2.

Mabee et al., "Updates on Softwood-to-Ethanol Process Development," *Appl. Biochem. Biotechnol.*, 2006, pp. 55-70, vol. 129-132.

Mortimer et al., "The Formation of Structure in The Spinning and Coagulation of Lyocell Fibers," *Cellulose Chemistry and Technology*, 1996, pp. 117-132, vol. 30.

Mortimer et al., "The Influence of Physical Process Parameters on the Structure Formation of Lyocell Fibers," *Cellulose Chemistry and Technology*, 1996, pp. 251-266, vol. 30.

Pastor et al., "Preparation of Activated Carbon Cloths From Viscous Rayon. Part I. Carbonization Procedures," *Carbon*, 1999, pp. 1275-1283, vol. 37.

Plaisantin et al., "Conversion of Cellulose Fibers Into Carbon Fibers: A Study of the Mechanical Properties and Correlation With Chemical Structure," *Composites Science and Technology*, 2001, pp. 2063-2068, vol. 61.

Rabinovich, "Ethanol Production From Materials Containing Cellulose: The Potential of Russian Research and Development," *Applied Chemistry and Microbiology*, 2006, pp. 1-26, vol. 42, No. 1.

Ragauskas et al., "The Path Forward for Biofuels and Biomaterials," *Science*, 2006, pp. 484-489, vol. 311.

Rodriguez-Reinoso et al., "Preparation of Activated Carbon cloths From Viscous Rayon Part III. Effect of Carbonization on the $CO_2$ Activation," *Carbon*, 2000, pp. 397-406, vol. 38.

Sarymsakov et al., "Study of Partial O-Alkylation of Cotton Cellulose," *Chemistry of Natural Compound*, 1997, pp. 337-339, vol. 33, No. 3.

Sun et al., "Hydrolysis of Lignocellulosic Materials for Ethanol Production: A Review," *Bioresource Technology*, 2002, pp. 1-11, vol. 83, No. 1.

Tashpulatov et al., "Enzymatic Production of Glucose Syrups From Cellulose-Containing Plant Wastes," *Chemistry of Natural Compounds*, 1997, pp. 273-275, vol. 33, No. 3.

Viswanathan et al., "Preparation of Biopolymer Fibers by Electrospinning From Room Temperature Ionic Liquids," *Biomacromolecules*, 2006, pp. 415-418, vol. 7.

Wilke et al., "Raw Materials Evaluation and Process Development Studies for Conversion of Biomass to Sugars and Ethanol," *Biotechnology and Bioengineering*, 1981, pp. 163-183, vol. 23.

Yue et al., "Preparation of Fibrous Porous Materials by chemical Activation 1. $ZnCl_2$ Activation of Polymer-Coated Fibers," *Carbon*, 2002, pp. 1181-1191, vol. 40.

Barthel et al., "Acylation and Carbanilation of Cellulose in Ionic Liquids," *The Royal Society of Chemistry/Green Chem*, 2006, pp. pp. 301-306, vol. 8.

Liebert et al., "Interaction of Ionic Liquids With Polysaccharides 5. Solvents and Reaction Media for the Modification of Cellulose," *BioResources*, 2008, pp. 576-601, vol. 3, No. 2.

Liu et al., "Preparation of Sugarcane Bagasse Cellulosic Phthalate Using an Ionic Liquid as Reaction Medium," *Carbohydrate Polymers*, 2007, pp. 17-25, vol. 68.

Murugesan et al., "Ionic Liquid-Derived Blood-Compatible Composite Membranes for Kidney Dialysis," *J. Biomed. Mater. Res. Part B: Appl. Biomater/InterScience*, 2005, pp. 298-304, vol. 79b.

Schlufter et al., "Efficient Homogeneous Chemical Modification of Bacterial Cellulose in the Ionic Liquid 1-N-Butyl-3-Methylimidazolium Chloride," *Macromolecular Rapid Communications/InterScience*, 2006, pp. 1670-1676, vol. 27.

Sheldrake et al., "Dicationic Molten Salts (Ionic Liquids) as Re-Usable Media for the Controlled Pyrolysis of Cellulose to Anhydrosugars," *Green Chemistry*, 2007, pp. 1044-1046, vol. 9.

Abbott et al., "O-Acetylation of Cellulose and Monosaccharides Using a Zinc Based Ionic Liquid," *Green Chemistry*, 2005, pp. 705-707, vol. 7, No. 10.

Arnautov et al., "Electrochemical Synthesis of Polyphenylene in a New Ionic Liquid," *Synthetic Metals*, 1997, pp. 295-296, vol. 84.

Augustine, et al., "Direct Solvents for Cellulose," *Cellulose Sources and Exploitation, Industrial Utilization, Biotechnology and Physico-Chemical Properties*, 1990, pp. 59-65.

Baeza et al., "Wood and Cellulosic Chemistry," $2^{nd}$ ed., 2001, Marcel Dekker Inc. New York. (*BOOK*).

Berger et al., "Alternative Variants of Dissolving Cellulose in New Organic Solvent Systems," *Cellulose Sources and Exploitation. Industrial Utilization, Biotechnology and Physico-Chemical Properties*, 1990, pp. 67-78.

Biswas et al., "Ionic Liquids as Solvents for Biopolymers: Acylation of Starch and Zein Protein," *Carbohydrate Polymers*, 2006, pp. 546-550, vol. 66.

Branco et al., "Preparation and Characterization of New Room Temperature Ionic Liquids," *Chemistry—A European Journal*, 2002, pp. 3671-3677, vol. 8, No. 16.

Byrne, "Carbonization of Wood for Advanced Materials Applications," *Carbon*, 1997, pp. 259-266, vol. 35, No. 2.

Chen et al., "Effect of Pressing on the Infrared Spectra of Single Cotton Fibers," *Applied Spectroscopy*, 2002, pp. 646-650, vol. 56, No. 5.

Collier et al., "Elongational Rheology of Polymer Melts and Solutions," *J. Appl Polym Sci*, 1998, pp. 2357-2367, vol. 69.

Collier et al., Rheology of Lyocell Solutions From Different Cellulose Sources, *Journal of Polymers and The Environment*, 2000, pp. 151-154, vol. 8, No. 3.

Deng et al., "Ionic Liquids as a Green Catalytic Reaction Medium for Esterifications," *Journal of Molecular Catalysis A: Chemical*, pp. 33-36, vol. 165, 2001.

Dupont et al., "Ionic Liquid (Molten Salt) Phase Organometallic Catalysis," *Chem. Rev.*, 2002, pp. 3667-3692, vol. 102.

Eggeman et al., "Process and Economic Analysis of Pretreatment Technologies," *Bioresource Technology*, 2005, pp. 2019-2025, vol. 96.

Firestone et al., "Lyotropic Liquid-Crystalline Gel Formation in a Room-Temperature Ionic Liquid," *Langmuir*, 2002, pp. 7258-7260, vol. 18.

Fort et al., "Use of Ionic Liquids in the Study of Fruit Ripening by High-Resolution $^{13}C$ NMR Spectroscopy: 'Green' Solvents Meet Green Bananas," *Chem. Commun.*, 2006, pp. 714-716.

Fort et al., "Can Ionic Liquids Dissolve Wood? Processing and Analysis of Lignocellulosic Materials With 1-n-butyl-3-Methylimidazolium Chloride," *Green Chemistry*, 2007, pp. 63-69, vol. 9. http://www.rsc.org/publishing/journals/GC/article.asp?doi=B607614a.

Gonzalez-Benito et al., "FTIR Imaging of the Dissolution of Polymers. 4. Poly(methyl methacrylate) Using a Cosolvent Mixture (Carbon Tetrachloride/Methanol)," *Macromolecules*, 2002, pp. 7361-7367, vol. 35.

Hinterstoisser et al., "Two-Dimensional Step-Scan FTIR: A Tool to Unravel the OH-Valency-Range of the Spectrum of Cellulose I," *Cellulose*, 1999, pp. 251-263, vol. 6.

Honglu et al., "Wood Liquefaction By Ionic Liquids," *Holzforschung*, 2006, pp. 509-512, vol. 60.

Huddleston et al., "Characterization and Comparison of Hydrophilic and Hydrophobic Room Temperature Ionic Liquids Incorporating the Imidazolium Cation," *Green Chemistry*, 2001, pp. 156-164, vol. 3.

Kaar et al., "Using Lime Pretreatment to Facilitate the Enzymatic Hydrolysis of Corn Stover," *Biomass and Bioenergy*, 2000, pp. 189-199, vol. 18.

Kataoka et al., "Changing Cellulose Crystalline Structure in Forming Wood Cell Walls," *Macromolecules*, 1996, pp. 6356-6358,vol. 29.

Kataoka et al., "FT-IR Microscopic analysis of Chaining Cellulose Crystalline Structure During Wood Cell Wall Formation," *Macromolecules*, 1998, pp. 760-764, vol. 31.

Kilpeläinen et al., "Dissolution of Wood in Ionic Liquids," *Journal of Agricultural and Food Chemistry*, 2007, pp. 9142-9148, vol. 55.

Kim et al., "Biocatalysis in Ionic Liquids: Markedly Enhanced Enantioselectivity of Lipase," *Organic Letters*, 2001, pp. 1507-1509, vol. 3, No. 10.

Kim et al., "Graphitization of Highly Crystalline Cellulose," *Carbon*, 2001, pp. 1051-1056, vol. 39.

Klemm et al., "Cellulose: Fascinating Biopolymer and Sustainable Raw Material," *Angew. Chem. Int. Ed.*, 2005, pp. 3358-3393, vol. 44.

Kondo, "The Assignment of IR Absorption Bands Due to Free Hydroxyl Groups in Cellulose," *Cellulose*, 1997, pp. 281-292, vol. 4.

Kragl et al., "Enzyme Catalysis in Ionic Liquids," *Current Opinion in Biotechnology*, pp. 565-571, vol. 13, 2002.

Kumar et al., "Effect of Reactive Atmosphere and Maximum Heat Treatment Temperature on Characteristics of Pyrolyzed Rayon Cloth," *Carbon*, 1997, pp. 703-706, vol. 35, No. 5.

Law et al., "Solvent-Free Route to Ionic Liquid Precursors Using a Water-Free Microwave Process," *Green Chemistry*, 2002, pp. 328-330, vol. 4.

Leveque et al., "An Improved Preparation of Ionic Liquids by Ultrasound," *Green Chemistry*, 2002, pp. 357-360, vol. 4.

Liu et al., "Enzymatic Hydrolysis of Cellulose Materials Treated With Ionic Liquid [BMIM] CI," *Chinese Science Bulletin*, 2006, pp. 2432-2436, vol. 51, No. 20.

Liu et al., "Synthesis and Application of Dictionic Ionic Liquids," *Journal of Chemical Technology and Biotechnology*, 2006, pp. 401-405, 2006, vol. 81, No. 3.

Macosko, *Rheology, Principles, Measurements and Applications*, Wiley-VCH, 1994. (BOOK).

Mohan et al., "Pyrolysis of Wood/Biomass for Bio-Oil: A Critical Review," *Energy & Fuels*, 2006, pp. 848-889, vol. 20.

Mosier et al., "Features of Promising Technologies for Pretreatment Lignocellulosic Biomass," *Bioresource Technology*, 2005, pp. 673-686, vol. 96.

Namboodiri et al., "An Improved Preparation of 1,3-Dialkylimidazolium Tetrafluoroborate Ionic Liquids Using Microwaves," *Tetrahedron Letters*, 2002, pp. 5381-5383, vol. 43.

Nimlos et al., "Enhancement of 1,2-Dehydration of Alcohols by alkali Cations and Protons: A Model for Dehydration of Carbohydrates," *Journal of Analytical and Applied Pyrolysis*, 2003, pp. 3-27, vol. 66.

Paillet et al., "New Biodegradable Films From Exploded Wood Solutions," *Journal of Applied Polymer Science*, 1990, pp. 427-433, vol. 40.

Patel et al., "Crystallization Kinetics During Polymer Processing—Analysis of Available Approaches for Process Modeling," *Polym. Eng. Sci.*, 1991, pp. 730-738, vol. 31, No. 10.

Patel et al., "Dynamics and Structure Development During High-Speed Melt Spinning of Nylon 6. II. Mathematical Modeling," *J. Appl. Polym. Sci.*, 1991, pp. 1671-1682, vol. 42.

Petrovan et al., "Rheology of Cellulosic N-Methylmorpholine Oxide Monohydrate Solutions," *Journal of Applied Polymer Science*, 2000, pp. 1369-1377, vol. 77.

Petrovan et al., "Rheology of Cellulosic N-Methylmorpholine Oxide Monohydrate Solutions of Different Degree of Polymerization," *Journal of Applied Polymer Science*, 2001, pp. 396-405, vol. 79.

Petrovan et al., "Elongational and Shear Rheology of Cellulosic and Lignocellulosic Solutions in N-Methylmorpholine Oxide Monohydrate," *Cell Chem. Technol.*, 2001, pp. 89-102, vol. 35, Nos. 1-2.

Phillips et al.,"Regenerated Silk Fiber Wet Spinning From an Ionic Liquid Solution," *J. Mater. Chem.*, 2005, pp. 4206-4208, vol. 15.

Rogers et al., "Ionic Liquids-Solvents of the Future?," *Science*, 2003, pp. 792-793, vol. 302.

Romanoschi et al., "Rheological Properties of Kenaf Lyocell Solutions," *Kenaf Properties, Processing and Products*, 1999, pp. 225-244.

Seddon, "Ionic Liquids for Clean Technology," *Journal of Chemical Technology and Biotechnology*, 1997, pp. 351-356, vol. 68, No. 4.

Sheldon, "Catalytic Reactions in Ionic Liquids," *Chem. Commun.*, 2001, pp. 2399-2407, vol. 23.

Swatloski et al., "Dissolution of Cellulose With Ionic Liquid," *Journal of the American Chemical Society*, 2002, pp. 4974-4975. vol. 124.

Treiber, "Trends in the Viscose and Dissolving Pulp Technology," *Cellulose Sources and Exploitation. Industrial Utilization, Biotechnology and Physico-Chemical Properties*, 1990, pp. 163-168.

Turner et al., "Production of Bioactive Cellulose Films Reconstituted from Ionic Liquids," *Biomacromolecules*, 2004, pp. 1379-1384, vol. 5.

Turner et al., "Ionic Liquid-Reconstituted Cellulose Composites as Solid Support Matrices for Biocatalyst Immobilization," *Biomacromolecules*, 2005, pp. 2497-2502, vol. 6.

Vygodskii et al., "Ionic Liquids as Novel Reaction Media for the Synthesis of Condensation Polymers,"*Macromolecular Rapid Communications*, pp. 676-680, vol. 23, No. 12, Aug. 21, 2002.

Wasserscheid et al., "Ionic Liquids-New 'Solutions' for Transition Metal Catalysis," *Angew.Chem., Int. ed.*, 2000, pp. 3772-3789, vol. 39.

Welton, "Room Temperature Ionic Liquids . Solvents for Synthesis and Catalysis," *Chem. Rev.*, 1999, pp. 2071-2083, vol. 99.

Wu et al., "Homogeneous Acetylation of Cellulose in a New Ionic Liquid," *Biomacromolecules*, 2004, pp. 266-268, vol. 5.

Wyman et al., "Coordinated Development of Leading Biomass Pretreatment Technologies," *Bioresource Technology*, 2005, pp. 1959-1966, vol. 96.

Xie et al., "Ionic Liquids As novel Solvents for the Dissolution and Blending of Wool Keratin Fibers," *Green Chem.*, 2005, pp. 606-608, vol. 7.

Xie et al., "Chitin and Chitosan Dissolved in Ionic Liquids as Reversible Sorbents of $CO_2$," *Green Chem.* 2006, pp. 630-633, vol. 8.

Xie et al., "Thorough Chemical Modification of Wood-Based Lignocellulosic Materials in Ionic Liquids," *Biomacromolecules*, 2007, pp. 3740-3748, vol. 8.

Zhang et al., "Novel Properties of Ionic Liquids in Selective Sulfur Removal From Fuels at Room Temperature," *Green Chemistry*, 2002, pp. 376-379, vol. 4.

Zhang et al., "1-Allyl-3methylimidazolium Chloride Room Temperature Ionic Liquid: A New and Powerful Nonderivatizing Solvent for Cellulose," *Macromolecules*, 2005, p. 8272, vol. 38, No. 20.

Ziabicki, *Fundamentals of Fiber Formation. The Science of Fiber Spinning and Drawing*, John Wiley & Sons, 1976. (BOOK).

Zhu et al., "Dissolution of Cellulose With Ionic Liquids and Its Application: A Mini-Review," *Green Chem.*, 2006, pp. 325-327, vol. 8.

* cited by examiner

PRODUCT PREPARATION AND RECOVERY FROM THERMOLYSIS OF LIGNOCELLULOSICS IN IONIC LIQUIDS

CROSS-REFERENCE TO RELATED APPLICATIONS

The present application claims priority to U.S. Provisional Patent Application No. 60/888,453, filed Feb. 6, 2007, which is incorporated herein by reference in its entirety.

FIELD OF THE INVENTION

The present invention is directed to methods of product production from biomass. More particularly, the invention is directed to methods of thermolysis of lignocellulosic materials and formation of various products.

BACKGROUND

Biomass is an increasingly popular starting material for production of a variety of materials. Ever growing energy demands and environmental concerns have particularly prompted much toward work developing convenient and efficient pathways for converting biomass to biofuels, valuable chemicals, and biomaterials.

Wood is the most abundant lignocellulosic resource on the planet. Although wood has long been used as raw materials for building, fuel, and various products, its use for converting to biofuel and producing valuable chemicals and biomaterials has only recently been considered in light of development of bioengineering and catalytic chemistry.

The complex structure of wood makes it insoluble in common molecular solvents, and preliminary chemical or physical treatment is thus necessary for further applications. Such preliminary treatments, especially chemical treatment, are generally undesirable because of the use and/or release of environmentally unfriendly chemicals. For example, NaOH and NaSH typically must be used to delignify wood in the kraft pulping manufacturing technology, which is the most popular method used in the paper industry.

For the traditional conversion of wood into composite-materials, wood flour is used or heterogeneous chemical modification is performed. Performing these processes is plagued by feedstock-degradation, as well as the unavoidable consumption of large amounts of energy and expensive chemicals. The traditional method to obtain biodegradable plastic and composites is heterogeneous graft modification, which has been disclosed in U.S. Pat. No. 5,424,382, U.S. Pat. No. 5,741,875, U.S. Pat. No. 5,852,069, and U.S. Pat. No. 6,013,774. These methods suffer drawbacks such as low efficiency and utilization of hazardous chemicals.

Lignin is a vastly under-utilized natural polymer. Commercial lignin is currently produced as a co-product of the paper industry, separated from trees by a chemical pulping process. Lignosulfonates (also called lignin sulfonates and sulfite lignins) are products of sulfite pulping. Kraft lignins (also called sulfate lignins) are obtained from the Kraft pulping process. Other delignification technologies use an organic solvent or a high pressure steam treatment to remove lignins from plants. Because lignins are very complex natural polymers with many random couplings, the exact chemical structure is not known, and the physical and chemical properties of lignin can differ depending on the extraction technology and the plant material from which it is extracted. For example, lignosulfonates are hydrophilic and Kraft lignins are hydrophobic. Lignin is typically used as a stabilizer (e.g. an antioxidant) for plastics and rubber, as well as in the formulation of dispersants, adhesives, and surfactants. Lignin or lignin derivatives have also been used in the production of fully biodegradable lignin-based composites.

Ionic liquids have recently received much attention as "green" (environmentally friendly), designable solvents, which are favorable in light of the growing realization of the need to protect the environment. Ionic liquids represent a new way of thinking with regard to solvents. The field is experiencing rapid growth, and offers a starting point for science, industry, and business to cooperate in the formation of a new paradigm of green chemistry and sustainable industry.

Ionic liquids offer a range of significant improvements upon conventional solvents, and also exhibit greater ability than water for solubilizing organic compounds. The unique structure of ionic liquids compared to traditional molecular solvents provides for many unique solubilization characteristics. For example, a range of ionic liquids applicable for the dissolution of cellulose are disclosed in U.S. Pat. No. 6,824,559. Furthermore, ionic liquids have shown good solubility characteristics for monomers or polymers and have been used to reconstitute advanced composites materials, as disclosed in International Publication WO 2005/098546.

Given the availability and renewability of biomass, particularly lignocellulosics, such materials would be highly useful as starting materials for the preparation of chemical raw materials. In particular, pyrolytic breakdown of biomass is a useful method for the breakdown of biomass in the production of a large number of chemical substances. The process of anaerobic pyrolysis converts organics to solid, liquid, and gas by heating it in the absence of oxygen. The amount of solid, liquid, and gaseous fractions formed is highly dependent on the process variables, as are the distribution of products within each solid, liquid, and gas phase produced. Although pyrolytic breakdown of biomass is a promising method for the production of many chemical compounds, there is still a need in the art for an efficient and effective method of carrying out such a process.

SUMMARY OF THE INVENTION

The present invention provides methods for the anaerobic pyrolysis of lignocellulosic materials to form a variety of useful chemical compounds and/or pyrolysis oils. The inventive methods are particularly made possible through the combination of the lignocellulosic material with an ionic liquid media. The combination can result in substantially swelling and at least partial dissolution of the lignocellulosic material, which beneficially can be performed under mild conditions. In specific embodiments, the methods of the invention include catalytic cracking and/or thermal decomposition of the solvated lignocellulosics to form useful products, such as liquid pyrolysis oils and a variety of chemical compounds. Thus, the inventive methods provide for the homogeneous conversion of lignocellulosic feedstocks into useful products.

Traditionally, wood or lignin pyrolysis occurs under highly heterogeneous and multi-phased conditions due to the nature of the solid lignocellulosic materials. Consequently, mass and heat transport are seriously limited, which in turn results in a rather non-homogeneous set of products being produced since reactions are occurring more rapidly on the surface of the solids, and product mass transfer is limited through the bulk of the solid material. The ability to do such pyrolytic chemistry under homogeneous conditions offers the possibilities of using homogeneous catalysis for such processes opening the door for the development of biomass catalytic cracking chemistry.

In a particular embodiment, the invention provides a method for pyrolysis of a lignocellulosic material. Preferably, the method comprises combining the lignocellulosic material with an ionic liquid to form a mixture. In the mixture, the lignocellulosic material can be partially or completely dissolved, can be swollen, or can be both partially dissolved and swollen. The mixture of the lignocellulosic material and the ionic liquid is subjected to pyrolytic conditions to form a fraction that comprises a recoverable product. The homogeneous pyrolysis conditions offer significantly improved yields of pyrolysis oils, which may be used (without further refining) as liquid fuels. Furthermore, the pyrolysis oils that emerge are rich in chemicals which, after further refining, could be used in specialized applications.

In particular embodiments, subjecting the mixture to pyrolytic conditions includes heating the mixture to a temperature of about 150° C. to about 300° C. In another embodiment, it comprises heating the mixture anaerobically. In a specific embodiment, the method comprises a distillation method.

The pyrolysis method can comprise formation of various fractions, including a distillate fraction, a tar fraction, and a char fraction. In certain embodiments, the recoverable product formed in the method comprises one or more commodity chemicals, such as levoglucosenone, levulonic acid, levulinic acid, 5-hydroxymethyl furfural, 2-furaldehyde (furfural), or 2-methylfurfural.

Various types of ionic liquids can be used in the invention. Non-limiting specific examples of useful ionic liquids include materials formed of a cation and an anion, wherein the cation is selected from the group consisting of imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, derivatives thereof, and combinations thereof, and wherein the anion is selected from the group consisting of halogens, phosphates, alkylphosphates, alkenylphosphates, $BF_4^-$, $PF_6^-$, $AsF_6^-$, $NO_3^-$, $N(CN)_2^-$, $N(SO_3CF_3)_2^-$, amino acids, substituted or unsubstituted carboranes, perchlorates, pseudohalogens, metal chloride-based Lewis acids, $C_{1-6}$ carboxylates, and combinations thereof.

In another aspect, the present invention is directed to a method of preparing a commodity chemical from a lignocellulosic material. In certain embodiments, the method comprises at combining the lignocellulosic material with an ionic liquid (e.g., at least partially dissolving and/or at least partially swelling the lignocellulosic material) to form a mixture, distilling the mixture, and recovering the commodity chemical. In particular, the commodity chemical can be selected from the group consisting of alcohols, phenols, aldehydes, organic acids, furans, catechols, and combinations thereof. In specific embodiments, the commodity chemical comprises levoglucosenone, levulonic acid levulinic acid, 5-hydroxymethyl furfural, 2-furaldehyde (furfural), or 2-methylfurfural.

DETAILED DESCRIPTION

Figure 1:
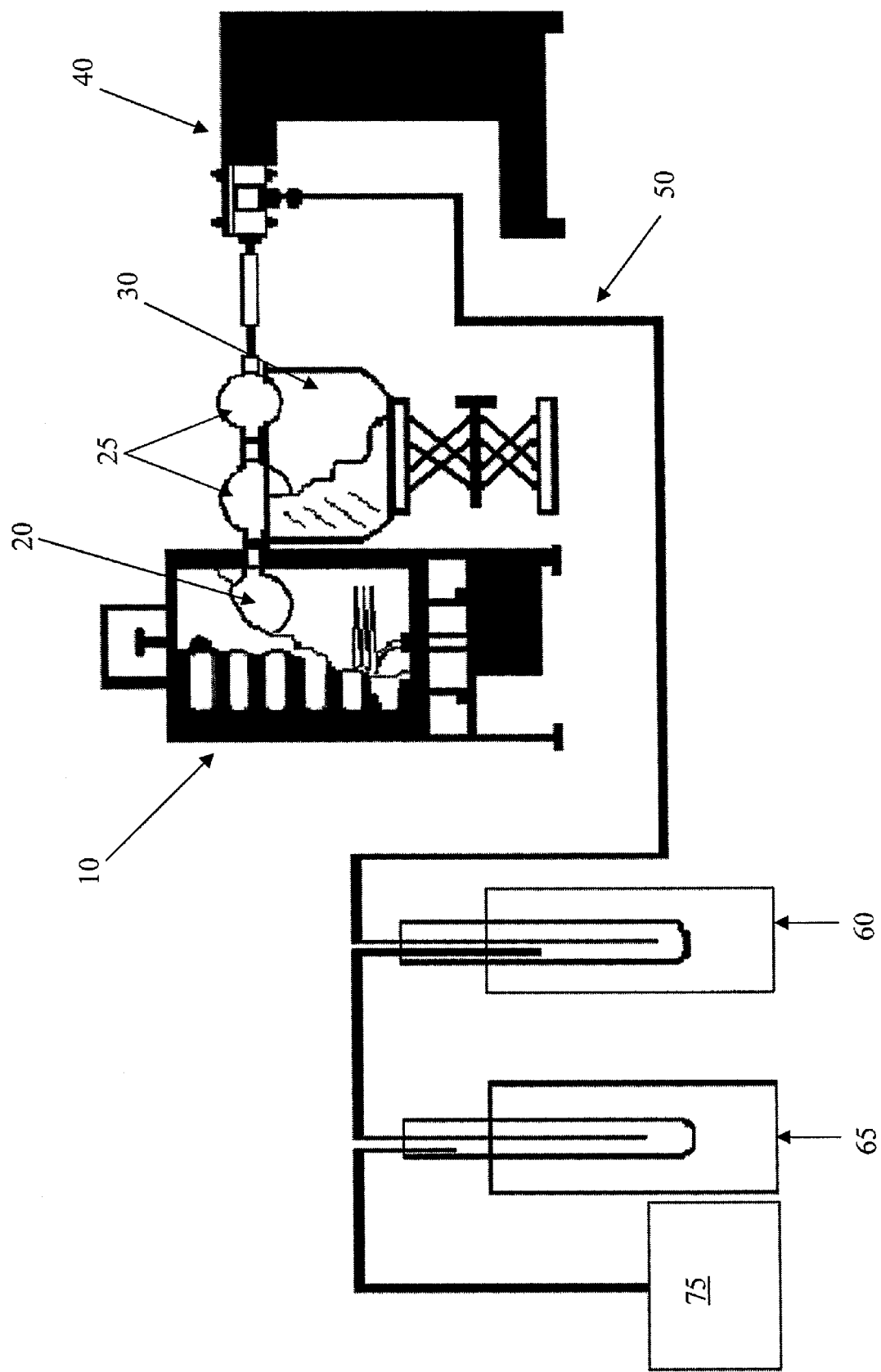
FIG. 1 is a schematic drawing of a distillation apparatus for use according to one embodiment of the invention.

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides methods that allow for the effective and efficient use of biomass, and particularly lignocellulosic materials, in the thermolytic production of a variety of useful products. Thermolysis is a chemical process for the decomposition of a starting (generally complex) substance into one or more ending (generally less complex) products through application of heat. Pyrolysis is typically recognized as a specific type of thermolytic process. Accordingly, the term thermolysis, as used herein, means the bringing about of any chemical change in a substance (such as cellulose, lignin, lignocellulose, woody materials, or biomass generally) through application of heat and specifically encompasses pyrolysis.

Generally, pyrolysis is understood to be the chemical decomposition of organic materials by heating in the absence of oxygen. In the pyrolysis of biomass, known methods typically rely on so-called "fast pyrolysis", which is usually required to achieve high liquid yields.

Fast pyrolysis is a thermal decomposition process that occurs at moderate temperatures with a high heat transfer rate to the biomass particles and a short hot vapor residence time in the reaction zone. Various types of reactors are known for use in such reactions, including bubbling fluid beds, circulating and transported beds, cyclonic reactors, and ablative reactors. Fast pyrolysis of biomass produces a liquid product and pyrolysis oil (or bio-oil) that can be readily stored and transported. Pyrolysis oil is a renewable liquid fuel and can also be used for production of chemicals. Fast pyrolysis has now achieved a commercial success for production of chemicals and is being actively developed for producing liquid fuels. Pyrolysis oils have been successfully tested in engines, turbines and boilers, and been upgraded to high quality hydrocarbon fuels although at present with unacceptable energetic and financial costs. The present invention may alter these relations due to the greater yields of pyrolysis oils obtained under the homogeneous pyrolysis conditions used.

Since pyrolysis is slightly endothermic, various methods have been proposed to provide heat to the reacting biomass particles: partial combustion of the biomass products through air injection; direct heat transfer with a hot gas, ideally product gas that is reheated and recycled; indirect heat transfer with exchange surfaces (e.g., wall, tubes); direct heat transfer with circulating solids; and solids transfer of heat between a burner and a pyrolysis reactor. All of the above methods have drawbacks, however, such as poor quality products, inability to provide sufficient heat with reasonable gas flow rates, difficulty in achieving good heat transfer on both sides of the heat exchange surface, and the shear complexity of the technology. The present invention is particularly advantageous in that the above problems are overcome through a pyrolytic method that uses distillation of the lignocellulosic material in combination with an ionic liquid such that the lignocellulosic material is highly swollen, partially dissolved, and/or completely dissolved.

The present invention is particularly useful in that pyrolysis is carried out using lignocellulosic material that is combined with an ionic liquid. The use of such material beneficially allows for the use of lower distillation temperatures than in known processes that do not incorporate the present combination steps. The combination with ionic liquid also overcomes the need for pretreatment with hazardous chemicals to prepare woody biomass for pyrolysis. The use of ionic liquids also increases the conversion efficiency and selectivity of the pyrolysis process, which beneficially leads to cost-effective production of valuable chemicals.

As further described below, the present invention also allows for recycling of the ionic liquids, which offers an environmentally friendly, low cost pathway for the energetically beneficial application of biopolymers. Moreover, the invention reduces waste materials and allows for the utilization of components that have previously been discarded. For example, black liquor lignin is presently burned and used as an energy source for many mills involved with biomass pyrolysis; however, the use of ionic liquid in lignin depolymerization can provide alternative and profitable applications for waste products, such as black liquor lignin.

Ionic Liquids

Generally, ionic liquids can be defined as compounds that are comprised entirely of ions and are liquids at temperatures of less than about 100° C., preferably less than about 85° C. Materials useful as ionic liquids according to the present invention also have a liquid range of up to about 300° C., which allows for good kinetic control. Such ionic liquids are excellent solvents for a wide range of inorganic, organic, and polymeric materials (high solubility generally meaning only small reactor volumes are necessitated and process intensification is provided). Preferentially, the ionic liquids can exhibit Brønsted, Lewis, and Franklin acidity, as well as superacidity, enabling many catalytic processes. They have no effective vapor pressure, are both hydrophilic and hydrophobic systems (further enhancing their industrial application), and are thermally stable up to about 200° C., preferably about 250° C., and more preferably about 300° C. Ionic liquids offer a wide variety of possible solvents allowing for process optimization (there are over a million ($10^6$) simple ionic liquids, and over a trillion ($10^{18}$) ionic liquid combinations). Ionic liquids are further beneficial in that they are relatively inexpensive (particularly in light of their facile recycling potential), easy to prepare, and commercially available.

As used in the present invention, ionic liquids generally comprise one or more anions and one or more cations. In preferred embodiments, the ionic liquids comprise organic cations created by derivatizing one or more compounds to include substituents, such as alkyl, alkenyl, alkynyl, alkoxy, alkenoxy, alkynoxy, a variety of aromatics, such as (substituted or unsubstituted) phenyl, (substituted or unsubstituted) benzyl, (substituted or unsubstituted) phenoxy, and (substituted or unsubstituted) benzoxy, and a variety of heterocyclic aromatics having one, two, or three heteroatoms in the ring portion thereof, said heterocyclics being substituted or unsubstituted. The derivatized compounds include, but are not limited to, imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, and combinations thereof. The basic cation structure can be singly or multiply substituted or unsubstituted.

The anionic portion of the ionic liquid can comprise an inorganic moiety, an organic moiety, or combinations thereof. In preferred embodiments, the anionic portion comprises one or more moieties selected from halogens, phosphates, alkylphosphates, alkenylphosphates, bis(trifluoromethylsulfonyl)imide ($NTf_2$), $BF_4^-$, $PF_6^-$, $AsF_6^-$, $NO_3^-$, $N(CN)_2^-$, $N(SO_3CF_3)_2^-$, amino acids, substituted or unsubstituted carboranes, perchlorates, pseudohalogens such as thiocyanate and cyanate, metal chloride-based Lewis acids (e.g., zinc chlorides and aluminum chlorides), or $C_{1-6}$ carboxylates. Pseudohalides are monovalent and have properties similar to those of halides (see, Schriver et al., Inorganic Chemistry, W. H. Freeman & Co., New York (1990) 406-407, which is incorporated herein by reference). Examples of pseudohalides useful according to the invention include cyanides, thiocyanates, cyanates, fulminates, and azides. Exemplary carboxylates that contain 1-6 carbon atoms are formate, acetate, propionate, butyrate, hexanoate, maleate, fumarate, oxalate, lactate, pyruvate and the like. Of course, such list is not intended to be an exhaustive listing of all possible anionic moieties possible according to the invention. Rather, a variety of further anionic moieties are also envisioned and encompassed by the present invention. For example, the invention also encompasses ionic liquids based on alkyl imidazolium or choline chloride anol-aluminum chloride, zinc chloride, indium chloride, and the like. Moreover, various further Lewis acid inorganic salt mixtures may be used (see *Green Chem.* (2005) 7, 705-707, which is incorporated herein by reference).

As noted above, a variety of ionic liquids can be prepared and used according to the present invention. In particular, any combination of the cations and anions noted above could be used. It is only necessary to combine one or more cations (such as those described above) with one or more anions (such as those described above) to form a material that is liquid under the conditions described herein. For example, a cation imidazolium moiety could be combined with an anionic halogen moiety to form a material that is liquid under the requisite conditions (e.g., 1-butyl-3-methyl-imidazolium chloride) and that is formed substantially completely of ionic moieties. Thus, it is clear that the present invention encompasses the use of a great diversity of ionic liquids. Specific, non-limiting examples of ionic liquids for use according to the invention include 1-butyl-3-methyl-imidazolium chloride ("BmimCl"); 1-allyl-3-methyl-imidazolium chloride ("AmimCl"); 1-ethyl-3-methyl-imidazolium chloride; 1-hydrogen-3-methyl-imidazolium chloride; 1-benzyl-3-methyl-imidazolium chloride ("BenzylmimCl"); 1-isopropyl-3-methyl-imidazolium chloride; 1-m-methoxybenzyl-3-methyl-imidazolium chloride ("MethoxyBenzylmimCl"); 1-m-methylbenzyl-3-methyl-imidazolium chloride ("MethylBenzylmimCl"); 1-benzyl-3-methyl-imidazolium chloride, and 1-methyl-3-benzyl-imidazolium dicyanamide ("BenzylmimDca"). These exemplary compounds are illustrated below in Formulas (1) through (6).

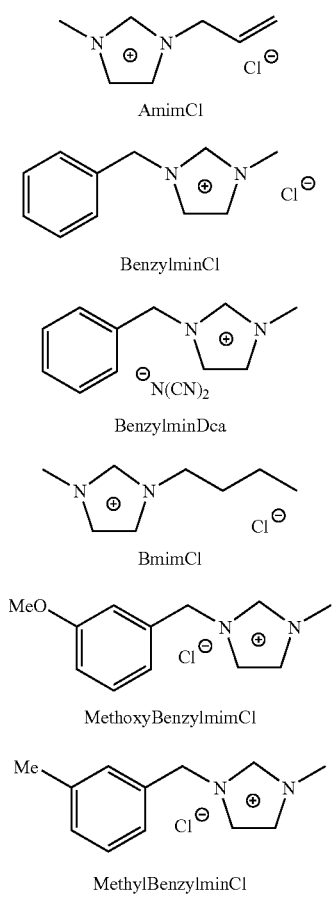

(1) AmimCl
(2) BenzylminCl
(3) BenzylminDca
(4) BmimCl
(5) MethoxyBenzylmimCl
(6) MethylBenzylminCl Exemplary methods for preparing ionic liquids of BenzylmimCl and BenzylmimDca are provided in Examples 1 and 2, respectively.

In still further embodiments, the present invention encompasses the uses of various ionic liquids incorporating phosphates as the anionic portion. Specific, non-limiting examples of such phosphate-containing compounds useful as ionic liquids include: bis[1,3-dimethylimidazolium] methylphosphate—Formula (7); tris[1,3-dimethylimidazolium] phosphate—Formula (8); 1,3-dimethylimidazolium diallylphosphate—Formula (9); 1,2,3-trimethylimidazolium dimethylphosphate—Formula (10); 1-benzyl-3-methylimidazolium dimethylphosphate—Formula (11); 1-vinyl-3-methylimidazolium dimethylphosphate—Formula (12); 1,3-dimethylimidazolium dimethylphosphate—Formula (13); 1,2,3-trimethylimidazolium methylhydrogenphosphate—Formula (14); and 1-allyl-3-methylimidazolium dimethylphosphate—Formula (15). Related compounds can be prepared by transesterification of the phosphate anion with an alcohol such as, allyl alcohol.

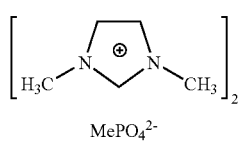

(7)

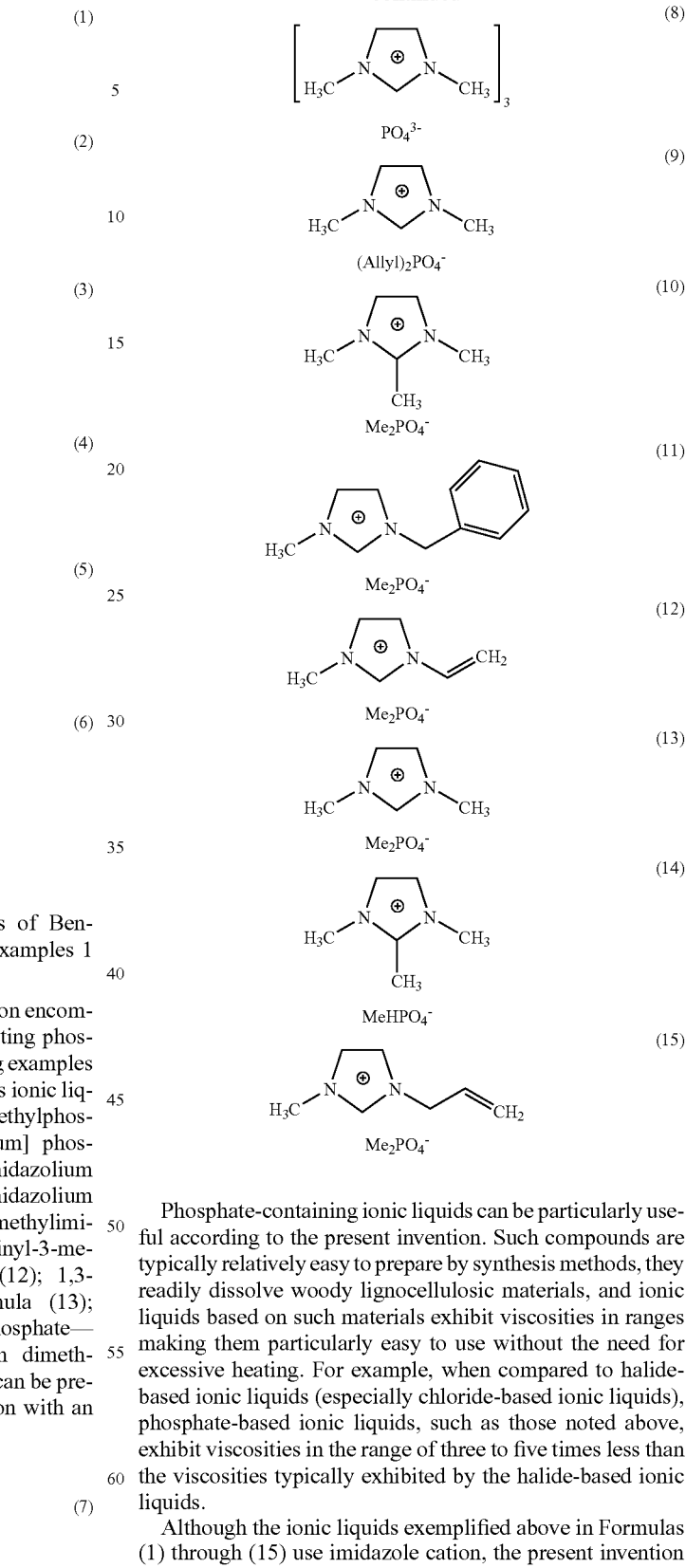

(8) $PO_4^{3-}$
(9) $(Allyl)_2PO_4^-$
(10) $Me_2PO_4^-$
(11) $Me_2PO_4^-$
(12) $Me_2PO_4^-$
(13) $Me_2PO_4^-$
(14) $MeHPO_4^-$
(15) $Me_2PO_4^-$ Phosphate-containing ionic liquids can be particularly useful according to the present invention. Such compounds are typically relatively easy to prepare by synthesis methods, they readily dissolve woody lignocellulosic materials, and ionic liquids based on such materials exhibit viscosities in ranges making them particularly easy to use without the need for excessive heating. For example, when compared to halide-based ionic liquids (especially chloride-based ionic liquids), phosphate-based ionic liquids, such as those noted above, exhibit viscosities in the range of three to five times less than the viscosities typically exhibited by the halide-based ionic liquids.

Although the ionic liquids exemplified above in Formulas (1) through (15) use imidazole cation, the present invention should not be limited only to the use of imidazole cationic moieties. Rather, as previously noted, the imidazole series of ionic liquids are only representative of the types of ionic liquids that can be used according to the invention. For example, in Formulas (1) though (15), the imidazole cation could be replaced with a pyridinium cation. Thus, the invention clearly also encompasses liquids formed of compounds as illustrated in Formulas (1) through (15) but wherein the cationic portion is a pyridinium cation. In other words, the invention particularly encompasses pyridinium chlorides and pyridinium phosphates. In specific embodiments, the ionic liquids useful according to the invention encompass allyl-methyl-pyridinium chloride, ethyl-methyl-pyridinium chloride, methyl-pyridinium chloride, benzyl-methyl-pyridinium chloride, isopropy-1-methyl pyridinium chloride, 1-m-methoxybenzyl-methyl-pyridinium chloride, 1-m-methylbenzyl-methyl-pyridinium chloride, or benzyl-methyl-pyridinium chloride. Likewise, it is clear that multiple pyridinium phosphate ionic liquids could be used based on the compounds of Formulas (7) through (15) wherein the imidazolium cation is substituted with a pyridinium cation. Based on this disclosure, it is also clear how to arrive at still further ionic liquids for use according to the invention. For example, useful ionic liquids could be based on an imidazolium cation or a pyridinium cation paired with any suitable anion as described above. Likewise, useful ionic liquids could be based on a chloride anion or a phosphate anion paired with any suitable cation as described above.

As previously pointed out, the ionic liquids used according to the invention can encompass one or more cations combined with one or more anions. In specific embodiments, the invention comprises the use of cation liquids formed of dicationic compounds. Dicationic materials can exhibit increased thermal stability and are thus particularly useful according to the present invention in light of the increased temperature used in the thermolytic processes. Dicationic ionic liquids can be prepared using any combination of cations and anions, such as those described above. For example, imidazoles and pyridines could be used in preparing dicationic ionic liquids in a similar manner as the ionic liquids described above using only a single cationic moiety.

In certain embodiments, the invention encompasses dicationic liquids having the structure provided below in Formulas (16) and (17)

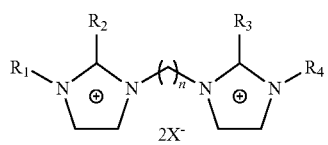

(16)

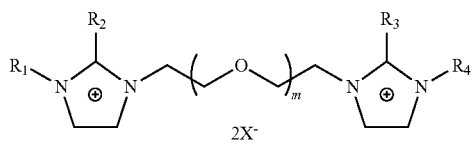

(17)

wherein n is an integer from 4 to 10; m is an integer from 1 to 4; X is a cationic moiety selected from the group consisting of Cl, Br, I, $NTf_2$, $(R)_2PO_4$, and $RHPO_4$; and R, $R_1$, $R_2$, $R_3$, and $R_4$ are independently selected from the group consisting of H, $C_{1-6}$ alkyl, $C_{1-6}$ alkenyl, and $C_{1-6}$ alkynyl. One specific example of a dicationic ionic liquid according to Formula (16) that is useful according to the present invention is the compound shown below in Formula (18).

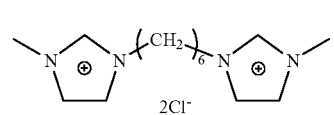

(18)

In further embodiments, the invention also encompasses dicationic liquids having the structure provided below in Formulas (19) and (20)

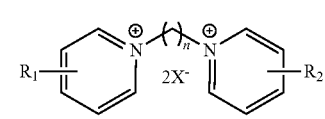

(19)

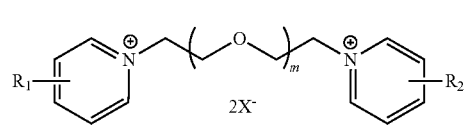

(20)

wherein n is an integer from 4 to 10; m is an integer from 1 to 4; X is a cationic moiety selected from the group consisting of Cl, Br, I, bis(trifluoromethylsulfonyl)imide ($NTf_2$), $(R)_2PO_4$, and $RHPO_4$; and R, $R_1$, and $R_2$ are independently selected from the group consisting of H, $C_{1-6}$ alkyl, $C_{1-6}$ alkenyl, and $C_{1-6}$ alkynyl. Dicationic compounds useful as ionic liquids according to the present invention can be prepared through synthesis methods known in the art. See, for example, *J. Chem. Technol Biotechnol.*, 81 (2006), p. 401-405, which is incorporated herein by reference in its entirety.

The invention also encompasses the use of various mixtures of ionic liquids. In fact, ionic liquid mixtures can be useful for providing ionic liquids having customized properties, such as viscosity. For example, BenzylmimCl is a relatively viscous ionic liquid; however, it viscosity can be significantly reduced by mixing with AmimCl. The viscosity of the ionic liquid mixture can thus be adjusted by varying the ratio between the more viscous component and the less viscous component.

Of course, in light of the above disclosure around suitable cationic moieties and suitable anionic moieties, the present invention also encompasses the many ionic liquids that can be prepared through suitable combinations of the disclosed cationic moieties and anionic moieties. Various further ionic liquids useful according to the invention are disclosed in U.S. Pat. No. 6,824,599, which is incorporated herein by reference.

Aromatic group-containing ionic liquids are particularly useful according to the invention. While not wishing to be bound by theory, it is believed that π-π interactions among the aromatic groups in lignin may account for the conformationally stable supermolecular structure of lignin. Thus, cationic moieties with an electron-rich aromatic π-system can create stronger interactions for polymers capable of undergoing π-π and n-π interactions. In particular, the aromatic character of the imidazolium ring of an ionic liquid cation offers potential π-π interactions with many aromatic moieties. Phenyl-containing ionic liquids provide particularly good solubilization of woody materials, as well as lignocellulosic materials generally.

Ionic liquids for use according to the invention can be synthesized according to the literature. Preferably, the ionic liquids are dried (e.g., at 100° C.) in a vacuum oven over a period of time, such as about 48 hours, prior to use. In one embodiment, the ionic liquid is formed of a material that is solid (e.g., crystalline) at ambient conditions but is liquid at increased temperature (such as greater than about 30° C., greater than about 40° C., greater than about 50° C., greater than about 75° C., greater than about 85° C., or greater than about 100° C.). Generally, the crystalline material can be placed in an appropriated container and heated to dissolution. See, for example, *Ionic Liquids in Synthesis*, Wasserscheid, P. and Weldon, T. (Eds.), Wiley Pub., which is incorporated herein by reference. Of course, the ionic liquid can also comprise a material that is liquid at ambient conditions (e.g., at a temperature around 20-25° C.). In particular, the present invention can encompass ionic liquids that are liquid at a temperature of about −10° C. to about 150° C., about 0° C. to about 150° C., or about 15° C. to about 150° C. Further, various ionic liquids are provided in prepared form, such as BASIONICS™ (available from BASF), which are imidazolium-based ionic liquids that are available in standard, acidic, basic, liquid-at-room-temperature, and low-viscosity forms.

Cellulosics and Lignocellulosics

Cellulose is a polysaccharide formed of 1,4-linked glucose units and is the primary structural component found in plants. Cellulose is the most abundant organic chemical on earth, and there is an estimated annual biosphere production of approximately $90 \times 10^9$ metric tons of the material. When measured in energy terms, the amount of carbon synthesized by plants is equivalent to about ten times the currently estimated global energy consumption.

Lignin is a compound that is most commonly derived from wood and is an integral part of the cell walls of plants. It is a three-dimensional amorphous natural polymer containing phenylpropane units that are tri- or tetra-substituted with hydroxyl groups and methoxyl groups. Lignin makes up about one-quarter to one-third of the dry mass of wood and generally lacks a defined primary structure. Lignocellulose is primarily a combination of cellulose, lignin, and hemicellulose. It is generally thought to be practically impossible to dissolve wood in its native form because the three-dimensional lignin network binds the whole wood architecture together. For example, in papermaking, the lignin network is fragmented under alkaline conditions, and cellulose is harvested as cellulose fibers. The insolubility of wood in common solvents has severely hampered the development of new methods for the efficient utilization of wood and its components. As described below, however, though the use of ionic liquids, it is possible to achieve complete dissolution of lignocellulosics, include wood in its native form.

Accordingly, the invention is particularly characterized in that a wide variety of cellulosics and lignocellulosics can be used as the biomass. For example, the biomass used in the invention can be derived from both herbaceous and woody sources. Non-limiting examples of herbaceous biomass sources useful according to the invention include tobacco, corn, corn stovers, corn residues, cornhusks, sugarcane bagasse, castor oil plant, rapeseed plant, soybean plant, cereal straw, grain processing by-products, bamboo, bamboo pulp, bamboo sawdust, and energy grasses, such as switchgrass, miscanthus, and reed canary grass.

The invention is particularly characterized by it efficacy toward the dissolution of different woody lignocellulosic materials. A variety of hardwoods and softwoods can be used in the invention in a multitude of different forms, such as chips, shreds, fibers, sawdust, and other physical forms. In a preferred embodiment, wood for use in the invention is in the form of dust or powder, such as ball milled powder.

Dissolution in ionic liquids according to the process of the present invention is particularly beneficial in that it has shown to be effective for use with softwoods. This is significant since the hydrolysis of softwood species is typically very low compared with hardwood species and other lignocellulosic materials when most of the current technologies are applied. Therefore, the method of the present invention provides a potential technique for production of various materials using softwood species, which are generally more abundant, and faster growing, than most hardwood species.

Softwood is a generic term typically used in reference to wood from conifers (i.e., needle-bearing trees from the order Pinales). Softwood-producing trees include pine, spruce, cedar, fir, larch, douglas-fir, hemlock, cypress, redwood and yew. Conversely, the term hardwood is typically used in reference to wood from broad-leaved or angiosperm trees. The terms "softwood" and "hardwood" do not necessarily describe the actual hardness of the wood. While, on average, hardwood is of higher density and hardness than softwood, there is considerable variation in actual wood hardness in both groups, and some softwood trees can actually produce wood that is harder than wood from hardwood trees. One feature separating hardwoods from softwoods is the presence of pores, or vessels, in hardwood trees, which are absent in softwood trees. On a microscopic level, softwood contains two types of cells, longitudinal wood fibers (or tracheids) and transverse ray cells. In softwood, water transport within the tree is via the tracheids rather than the pores of hardwoods.

Still further, various lignocellulosics generally regarded as "waste" materials can be used according to the present invention. For example, materials that have heretofore been discarded or thought of little value, such as corn stover, rice straw, paper sludge, and waste papers, can all be used as a lignocellulosic starting material according to the present invention. Particularly, it is possible to use various grades of paper and pulp, including recycled paper, which include various amounts of lignins, recycled pulp, bleached paper or pulp, semi-bleached paper or pulp, and unbleached paper or pulp. Such papers and pulps can be of various lignin contents and origins.

The present invention may be described herein in terms of lignocellulosic materials; however, such term does not necessarily exclude the use of materials that may more specifically be defined as cellulosic materials or ligninic materials. Rather, the term lignocellulosic is intended to broadly refer to biomass that may be primarily formed of cellulose, lignin, or lignocellulose. Thus, as used herein, lignocellulosic can mean materials derived from woody sources, grassy sources, and other plant sources generally. Specifically, lignocellulosic can mean a material comprised partly or mainly of lignin, cellulose, or lignocellulose.

Thermolysis Process

The thermolysis of lignocellulosics (or in specific embodiments, the pyrolysis of lignocellulosics) can be carried out using a variety of methods and apparatuses. For descriptive purposes, the thermolysis of woody materials is described herein in connection to a distillation apparatus. Of course, the invention is not so limited, but rather encompasses any other method whereby thermolysis of a biomass feedstock, particularly lignocellulosics and especially woody materials, can be effected on such material combined with an ionic liquid to effect swelling and/or dissolution of the lignocellulosic material.

In one embodiment of the invention, the anaerobic pyrolysis of lignocellulosic material is carried out using a Kugelrorh short-path distillation apparatus. A short-path distillation is a distillation technique that involves the distillate traveling a short distance, often only a few centimeters. A classic example would be a distillation involving the distillate traveling from one glass bulb to another, without the need for a condenser separating the two chambers. This technique is often used for compounds which are unstable at high temperatures. Advantages are that the temperature of the boiling liquid does not have to be much higher than the boiling point of the distilling substance, and the gases only have to travel a short distance while in the gas-phase before they can be cooled again to a lower temperature. In a Kugelrohr distillation, a short path distillation apparatus is typically used (generally in combination with a vacuum) to distill high boiling (e.g., >300° C.) compounds. The apparatus typically consists of an oven in which the compound to be distilled is placed, a receiving portion which is outside of the oven, and a means of rotating the sample. The vacuum is normally generated by using a high vacuum pump. One example of distillation apparatus useful according to the present invention is provided in FIG. 1.

The apparatus illustrated in FIG. 1 comprises a heated air bath 10 that is partially cut away to make visible the sample heating flask 20 contained therein. The apparatus further comprises two receiving flasks 25 to receive the distillates. In particular, tar components may be collected in the receiving flasks 25. As illustrated in FIG. 1, the receiving flasks 25 are in a cooling bath 30 (shown partially cut away to reveal the complete cooling flask 25), which can comprise any means useful for cooling the receiving flasks. In certain embodiments, a cooling bath can be completely dispensed with. In the embodiment of FIG. 1, the apparatus also comprises a motor drive 40 for rotating the sample heating flask 20 and the receiving flasks 25. In other embodiments, rotating means can be connected only to the sample heating flask 20. From the receiving flasks 25, the distillate travels through a series of tubing 50 to one or more condensing units. In FIG. 1, a first condensing unit 60 and a second condensing unit 65 are shown. In the first condensing unit 60 is a combination of acetone and solid CO2. In the second condensing unit 65 is liquid nitrogen. Multiple condensing units can be particularly useful for isolating condensates in differing boiling ranges. To facilitate movement of the distillates, a vacuum pump 75 is provided at the end of the tubing.

To carry out thermolysis according to the invention, the lignocellulosic materials are combined with an ionic liquid to change the structure of the lignocellulosic material through swelling and at least partial dissolution of the lignocellulosic material. Dissolution of the lignocellulosic material can be carried out under a variety of conditions. For example, in specific embodiments, the ionic liquid used in the dissolution is in the substantial absence of water (i.e., is substantially free of water). In other embodiments, the ionic liquid is in the substantial absence of a nitrogen-containing base (i.e., is substantially free of any nitrogen-containing base). The phrases "substantial absence" and "substantially free" are used synonymously to mean that the ionic liquid comprises less than about 5% by weight water and/or less than about 5% by weight of a nitrogen-containing base. In one embodiment, the ionic liquid comprises less than about 5% by weight water. In another embodiment, the ionic liquid comprises less than about 5% by weight of a nitrogen-containing base. In yet another embodiment, the ionic liquid comprises less that about 5% by weight of water and nitrogen-containing base combined. In particularly preferred embodiments, the ionic liquid comprises less than about 1% by weight water and/or nitrogen-containing base. In specific embodiments, the ionic liquid is completely free of water, is completely free of nitrogen-containing base, or is completely free of both water and a nitrogen-containing base.

The lignocellulosic material can be dissolved in the ionic liquid prior to being subjected to thermolytic conditions. For example, the lignocellulosics can be added to the ionic liquid media and the admixture can be agitated until dissolution is complete. Heat can be provided to the mixture in certain embodiments, such as in an ultrasonic bath, an oil bath or, by microwave irradiation. The ionic liquid is preferably molten at a temperature of less than about 150° C., more preferably less than about 100° C., more preferably less than about 85° C. Such temperatures are likewise sufficient to dissolve the lignocellulosics in the ionic liquid.

Beneficially, according to the present invention, dissolution and thermolysis can take place in the same container (i.e., in a single step reaction). For example, in certain embodiments, it is possible to simply add together in a suitable reaction vessel the ionic liquid and the lignocellulosic material and then begin increasing the temperature of the vessel, preferably under continuous agitation. The increased temperature and the agitation cause the lignocellulosic material to become dissolved and thus be in a state where thermolytic reaction can take place. That the ionic liquid provides a solution medium and a thermolysis medium is highly beneficial in that it is not necessary to perform multiple process steps using different reactor set-ups and reaction conditions. Rather, according to the present invention, the lignocellulosic material can be solvated and under thermolysis in a single step process using a single reactor set-up. Thus, although dissolution and thermolysis may be described herein separately, it is understood that both dissolution and thermolysis can take place in the same reaction vessel. For example, once all reactants are placed in the reaction vessel, appropriate conditions can be applied to cause dissolution of the lignocellulosic material in the ionic liquid, and the conditions can thereafter be adjusted to begin thermolysis. In certain embodiments, the reaction conditions can undergo a continuous variation so that dissolution proceeds continuously into thermolysis.

Preferably, dissolution is carried out such that the reaction mixture of the ionic liquid and the lignocellulosic material is maintained under an inert atmosphere. In one embodiment, the dissolution is carried out under an argon atmosphere. In another embodiment, dissolution is carried out under a nitrogen atmosphere. This is particularly useful to avoid introduction of water into the ionic liquid. Reaction according to the invention can be carried out, however, with the reaction vessel open to the atmosphere so long as relative humidity is low so as to avoid the presence of excess water in the air around the reaction vessel. In specific embodiments, the reaction is carried out under a vacuum. This can be useful to augment dissolution, as well as drive off any water that may be present and to allow for further increased reaction temperatures to reduce the viscosity of the ionic liquid.

The lignocellulosics, once solvated by the ionic liquid, are in a form that is more readily subject to further action, such as thermolysis. Complete dissolution of lignocellulosic materials, including wood in its native form, can be achieved by simply mixing the lignocellulosic material with the ionic liquid. Preferably, the mixing is carried out at a temperature suitable to maintain the liquid state of the ionic liquid. In certain embodiments, the mixing is carried out at a temperature of about 50° C. to about 150° C., about 60° C. to about 140° C., about 70° C. to about 130° C., or about 80° C. to about 120° C. Although increasing temperature tends to reduce the time to total dissolution, it is possible to obtain total dissolution at even ambient temperature. For example, when wood sawdust is gently homogenized with AmimCl in a mortar and the sample is subsequently transferred into a test tube (under argon), the mixture slowly turns to liquid (complete dissolution) over time. Temperature can also be influenced by the ionic liquid composition. Ionic liquids with lower viscosities can be used at lower temperatures, while ionic liquids with higher viscosities can require higher temperatures. Of course, since the present invention allows for a single reactor set-up to carry out both dissolution and thermolysis, a wide variety of ionic liquids having various viscosities and temperature profiles can be used.

Preferably, the dissolution reaction parameters are coordinated so that complete dissolution is achieved in a desired time. For example, in certain embodiments, complete dissolution is achieved in a time of less than about 48 hours, less than about 36 hours, less than about 24 hours, less than about 18 hours, less than about 12 hours, less than about 10 hours, less than about 8 hours, less than about 6 hours, less than about 4 hours, less than about 2 hours, or less than about 1 hour. Of course, the time to complete dissolution can vary according to the various embodiments of the invention and can be reduced, as desired, through manipulation of the reaction parameters, such as temperature and degree of agitation.

Dissolution can particularly be facilitated through application of mechanical stirring using any known stirring means. Achieving complete dissolution of even wood fibers has been demonstrated using a hot stage optical microscopy investigation of Norway spruce sawdust sample in AmimCl. Optical photomicrographic analysis of wood dissolution as a function of time at a temperature of 120° C. indicated that, after four hours, any visible fibrous material was completely dissolved by the ionic liquid.

Depending upon the nature of the lignocellulosic material, it may be further useful for dissolution to be carried out with further considerations. For example, the dissolution rate of wood can be dependant upon the particle size of the wood. It is believed that the complex and compact structure of the wood cell wall between the lignin, cellulose, and hemicellulose would essentially inhibit the diffusion of the ionic liquid into its interior, resulting in only a partial dissolution of wood chips. Accordingly, solubility of lignocellulosics, particularly wood in its native form, can be increased through sample preparation. Solubilization efficiency of lignocellulosic materials in ionic liquids can be defined, in certain embodiments, as follows: ball-milled wood powder>sawdust>thermomechanical pulp fibers>wood chips. For example, the dissolution of fine sawdust (Norway spruce, particle size=0.1-2 mm) in ionic liquid has been shown to take place within a few hours, even under ambient conditions.

The solubility limit of lignocellulosics in the ionic liquids can vary depending upon the choice of ionic liquid, the choice of lignocellulosic material, and the physical state of the lignocellulosic material. The present invention is particularly beneficial in that increased concentrations of lignocellulosic material can be utilized without diminishing the beneficial outcomes of the invention. In certain embodiments, it is possible according to the invention to form solutions having a lignocellulosic concentration of up to about 20% by weight, based upon the overall weight of the solution. In other embodiments, it is possible to form solutions having lignocellulosic concentrations of up to about 18% by weight, up to about 16% by weight, up to about 14% by weight, up to about 12% by weight, up to about 10% by weight, up to about 9% by weight, up to about 8% by weight, up to about 7% by weight, up to about 6% by weight, or up to about 5% by weight, based on the overall weight of the solution. These exemplify the ranges wherein complete dissolution of the lignocellulosic material in ionic liquid can be obtained. Table 1 provides examples of the dissolution behavior of various wood-based lignocellulosic materials in different imidazolium-based ionic liquids.

TABLE 1

| Sample | Ionic Liquid | Wood Sample Form | Conditions | Wt. % |
|---|---|---|---|---|
| 1 | BmimCl | Wood chips | 130° C., 15 h | ** |
| 2 | AmimCl | Ball-milled Southern pine powder | 80° C., 8 h | 8% |
| 3 | AmimCl | Norway spruce sawdust | 110° C., 8 h | 8% |
| 4 | AmimCl | Norway spruce sawdust | 80° C., 24 h | 5% |
| 5 | BmimCl | Norway spruce sawdust | 110° C., 8 h | 8% |
| 6 | AmimCl | Norway spruce TMP | 130° C., 8 h | 7% |
| 7 | BmimCl | Norway spruce TMP | 130° C., 8 h | 7% |
| 8 | AmimCl | Southern pine TMP | 110° C., 8 h | 2% |
| 9 | AmimCl | Southern pine TMP | 130° C., 8 h | 5% |
| 10 | BmimCl | Southern pine TMP | 130° C., 8 h | 5% |
| 11 | BenzylmimCl | Southern pine TMP | 130° C., 8 h | 5% |
| 12 | BenzylmimCl | Norway spruce TMP | 130° C., 8 h | 5% |
| 13 | MethoxyBenzylmimCl | Southern pine TMP | 130° C., 8 h | 5% |
| 14 | MethoxyBenzylmimCl | Southern pine TMP | 130° C., 8 h | 2% |
| 15 | BenzylmimDca | Southern pine TMP | 130° C., 8 h | 2% |

** Sample showed only partial solubility

Since complete solubilization of the lignocellulosic material in the ionic liquid is not essential to the thermolysis methods of the invention, it is possible to use even greater concentrations of lignocellulosic materials. The occurrence surface swelling of the lignocellulosic material allows for the progressive reactive dehydration and dissolution of the lignocellulosic substrate with the concomitant production of various chemicals which are pulled out under vacuum from the reaction mixture. Thus, in certain embodiments, the methods of the invention can be carried out using solutions of lignocellulosic material in ionic liquid having concentrations of up to about 40% by weight, up to about 35% by weight, up to about 30% by weight, or up to about 25% by weight.

The present invention clearly evidences the ability of ionic liquids to dissolve lignocellulosic material and change the basic structure of the lignocellulosic material. However, as pointed out above, complete dissolution of lignocellulosic materials can be dependant upon reaction conditions, particularly include the concentration of the lignocellulosic material in the ionic liquid. Moreover, since the ionic liquid acts on the lignocellulosic material to promote swelling, which also substantially "re-structures" the lignocellulosic material in a manner that facilitates pyrolysis according to the invention, complete dissolution is not required according to the invention. Thus, it is understood according to the invention that, when combined with ionic liquid, a lignocellulosic material will undergo a physical change. That physical change is expected to include, at least to some extent, dissolution of the lignocellulosic material. In certain embodiments, dissolution may not be complete; however, the concomitant swelling of the remaining portions of the lignocellulosic material put the entire content of the lignocellulosic material in a condition that facilitates pyrolysis according to the invention. Thus, while the invention may be described herein in terms of "dissolution", "dissolving", "salvation", or being "solvated", such terms are intended to encompass complete dissolution of the lignocellulosice material, as well as partial dissolution and swelling.

The highly crystalline character of cellulose in wood is driven by a set of regular intermolecular and intramolecular hydrogen-bonding interactions that when coupled with the three-dimensional network character of lignin and its possible covalent linkages with the carbohydrates are primarily responsible for the complex and compact structure of wood. For example, π-π interactions among the aromatic groups in lignin have been suggested as accounting for the conformationally stable supermolecular structure of lignin. Ionic liquids have a more complex solvent behavior compared with traditional solvents, and that complex solvent behavior can include π-π, n-π, hydrogen bonding, dipolar, and ionic/charge—charge types of interactions between the ionic liquids and their solutes. It has been reported that although the Bmim cation does not have the analogous electron aromatic system, the chloride anion (with nonbonding electrons), in combination with the Bmim cation, forms an ionic liquid that exhibits the ability to interact with π-systems of certain molecules. For example, the active chloride ions in ionic liquids, such as BmimCl and other ionic liquids described herein, may disrupt the hydrogen-bonding interactions present in wood, allowing it to diffuse into the interior of the wood. Thus, the use of ionic liquids according to the present invention allows for the achievement of reactions not heretofore possible because of the excellent swelling of lignocellulosic materials provided by the ionic liquids, even at high concentrations of the lignocellulosic materials.

The lignocellulosic material dissolved in the ionic liquid can be placed a distillation apparatus as described above. Of course, various further types of distillation apparatuses can also be used. Preferably, the solution of solvated lignocellulosic material in ionic liquid is heated for a time sufficient to distill the desired components. Therefore, distillation time can vary depending upon the desired end product, the distillation volume, and the distillation temperature. In certain embodiments, the distillation is carried out until substantially only char remains in the distillation container. Recovered products can be in the form of distillates or can be separated from a tar fraction that is obtained. In the apparatus of FIG. 1, for example, a tar fraction can be formed in the receiving flasks 25.

In specific embodiments, the method of the invention is further beneficial in that pyrolysis can be carried out at temperatures much lower than typically required in known methods for biomass pyrolysis. This is particularly possible because of the swelling effect on the lignocellulosic material provided by the ionic liquid. In specific embodiments, pyrolysis is carried out at temperatures in the range of about 100° C. to about 300° C., preferably about 125° C. to about 250° C., more preferably about 150° C. to about 225° C. Of course, in terms of energy expenditures, it is desirable to achieve pyrolysis using temperatures as low as possible. In specific embodiments, pyrolysis can be carried out at temperatures of less than about 250° C., less than about 225° C., less than about 200° C., or less than about 175° C.

In specific embodiments, the methods of the invention can be described as being carried out under pyrolytic conditions. As used herein, pyrolytic conditions can specifically mean a temperature sufficient to cause pyrolysis of the sample. Preferably, such a temperature is as described above. Of course, in light of the benefits provided by the dissolution in ionic liquid, a pyrolysis temperature according to the present invention can be significantly less than a pyrolysis temperature carried out on a material not solvated with an ionic liquid. Pyrolysis conditions can also include the application of a vacuum.

In one embodiment, pyrolysis is carried out anaerobically (i.e., in the substantial absence of oxygen). Thus, pyrolytic conditions according to the invention can mean being carried out in the substantial absence of oxygen or in the complete absence of oxygen. As previously pointed out, this can be accomplished by performing the pyrolysis in an inert environment, such us under nitrogen or under another non-reactive gas, such as argon. Application of a vacuum can also function to create conditions being in the substantial absence of oxygen.

The dissolution of lignocellulosic materials in ionic liquids is also beneficial for improving the yield of desired fractions during thermolysis. Typically, thermolysis of a lignocellulosic material can be expected to yield a distillate fraction, a tar fraction, and a char fraction. In one evaluation, the percent yield for each fraction was determined for a woody lignocellulosic material with and without being dissolved in ionic liquid. The results of the evaluation are described below in Example 6.

In addition to the benefit derived simply from the use of an ionic liquid for dissolving the lignocellulosic material, the composition of the products obtained by the thermolytic methods of the invention also can be varied by altering the structure of the ionic liquid used. Still further product variations can be obtained by specifically including or excluding acidic catalysts in the mixture. For example, dehydration reactions typically require acidic catalysts. As such, the homogeneous conditions offered by the ionic liquids in the present invention can facilitate development of biomass catalytic cracking processes.

Non-limiting examples of catalytic substances useful according to the present invention include various sources of Lewis acidity possessing mineral characteristics. For example various mineral acids, such as phosphoric acid, sulfuric acid, hydrochloric acid, nitric acid, boric acid, or hydrofluoric acid, could be used as a catalyst according to the invention. Specific further examples include aluminum and zinc chlorides and mineral variations thereof. Organic acids, such as p-toluene sulfonic acid and variants thereof are also particularly useful. It can be particularly useful to include substances that promote the dehydration of cellulose toward the formation of anhydrous sugars.

Although the methods of the invention are described herein in terms of thermolysis or pyrolysis, such terms are not meant to be overly limiting of the scope of the invention. For example, in certain embodiments, the present invention can generally be described as a method of catalytically cracking lignocellulosic materials. This term can particularly describe the methods of the invention whereby various catalysts are used to dehydrate cellulose and "pyrolytically crack" lignin to form lower phenolic homologues.

The methods of the invention result in the formation of a recoverable product. As used herein, the term "recoverable product" is intended to mean a product that is formed by the pyrolytic reactions of the invention and that is derived from the underlying lignocellulosic material. As noted above, the methods of the invention can result in the formation of various fractions, such as a distillation fraction, a tar fraction, and a char fraction. Accordingly, the recoverable product can be present in any of the fractions formed during the pyrolysis.

The invention is particularly beneficial in that it provides efficient and effective pathways for the production and isolation of a number of useful chemicals. Accordingly, in certain embodiments, the recoverable product of the invention comprises a chemical compound, particularly a chemical compound present in a distillation fraction. Non-limiting examples of the types of chemicals that can be obtained according to the present invention include alcohols (particularly various substituted and unsubstituted phenols), aldehydes (particularly aromatic aldehydes), organic acids, various furans, and catechols. In one embodiment, the methods of the invention are particularly useful for preparing Levoglucosenone (LGO). In another embodiment, the methods of the invention are further useful for preparing levulinic acid.

Levoglucosenone is a bicyclic enone molecule that is an important and efficient chiral starting material for the synthesis of many analogs of complex natural products. LGO exhibits high chemical reactivity in light of its conjugated system and is particularly useful in the synthesis of a variety of natural product targets that require stereoselective coupling with the sugar unit. Overall, LGO can be regarded as the most prominent carbohydrate molecule used in conjugate addition to achieve complete stereoselectivity of the addition and generally in the synthetic approach to 1,4- and 1,2-thiodisaccharides. These stereoselective, one-step synthetic approaches to (1,4)-3-deoxy-thiodisacharides and (1,2)-3-deoxy-thiodisaccharides are classical examples of exploiting the excellent functionality of both levo- and isolevoglucosenone enones for the creation of pharmaceutical precursors.

Although the traditional method of cellulose pyrolysis for the production of LGO is still a viable procedure, synthetic methods utilizing various, and cheap, starting carbohydrate precursors are highly competitive and cost-effective alternatives. For this reason, advances in catalytic cellulose pyrolytic methods for the production of LGO, such as provided herein, are highly desirable.

Levulinic acid is a highly useful precursor that can also be prepared according to embodiments of the present invention, particularly when the pyrolytic methods are carried out under acid catalysis conditions. Levulinic acid is a versatile chemical since it can function as an intermediate in the preparation of various further compounds. One particular derivative of levulinic acid, methyl tetrahydrofuran (MTHF), is known to be a low volatility gasoline extender. In addition, various industrial chemicals can be manufactured from levulinic acid including, but not limited to, tetrahydrofuran, 1,4-butanediol, diphenolic acid, succinic acid, gamma butyrolactone, angelicalactone, and N-methylpyrrolidone. Existing domestic markets for such chemicals are presently estimated to be in excess of approximately one billion dollars per year. Thus, it is clear that the present invention is particularly beneficial as providing a new and efficient technology that effectively utilizes lignocellulosic materials (including waste materials) by converting them into high-value added products.

The present invention can thus provide a method for the preparation of a variety of commodity chemicals. As used herein, the term "commodity chemical" refers to any chemical compound that has stand-alone value as a product sold in commerce. Commodity chemicals can include chemicals that are used directly by consumers or chemicals that are used as reactants or intermediates in the preparation of other chemicals or products. In specific embodiments, the methods of the present invention make possible the preparation of a wide variety of commodity chemicals that are themselves high-value added products or are used in the preparation of other high-value added products. Specific examples of such chemicals that can be prepared according to the present invention include, but are not limited to, levulinic acid, 5-hydroxymethyl furfural, 2-furaldehyde (furfural), 2-methylfurfural, and levoglucosenone. Of course, these are only examples of the variety of valuable chemicals that can be prepared according to the methods of the present invention.

In specific embodiments, the inventive method for the preparation of commodity chemicals can generally encompass any of the methods steps described herein. For example, the methods can comprise dissolving a lignocellulosic material using an ionic liquid and subjecting the lignocellulosic material to conditions suitable to result in pyrolysis and/or cracking of the lignocellulosic material. In particular, the method can comprise distilling the at least partially solvated lignocellulosic material under pyrolytic conditions, as described herein.

The invention is further characterized in that the ionic liquid media can be recovered and reused. After completion of the pyrolysis steps, the remaining portions of the distillation mixture (for example, the remaining char) can be further treated to recover any remaining ionic liquid, as well as further components. In one method, the char is dissolved in water and separated to obtain a water phase and a solid phase. The solid phase can be treated to recover wood residuals. The water phase can be treated with alcohol to obtain an alcohol phase and a water phase, and the ionic liquid can be recovered from the water phase, such as by evaporating the water and drying the ionic liquid.

Figure 2:
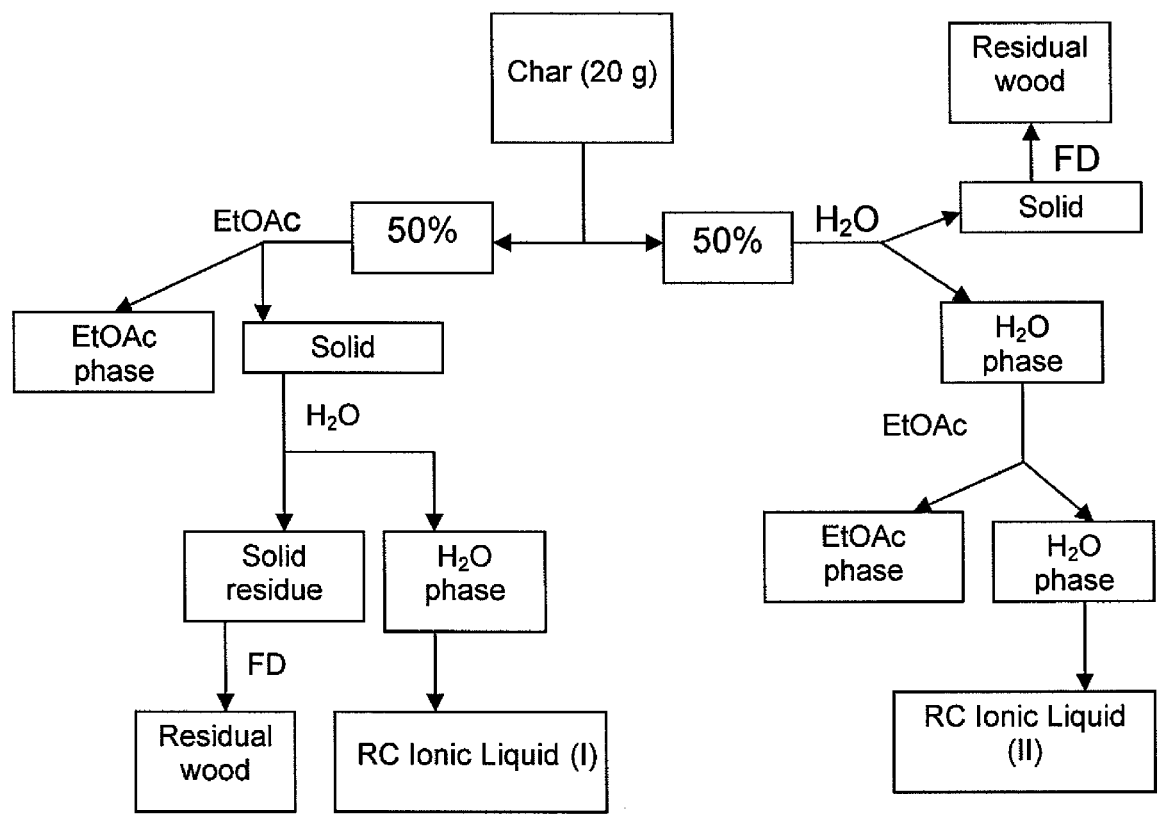
FIG. 2 is a flowchart describing two flow paths for recycling ionic liquid media according to one embodiment of the invention.

In another method, the char is dissolved in alcohol to obtain a solid residue and an alcohol phase. The solid residue can be dissolved in water to obtain a solid phase and a water phase. The solid phase can be treated to recover wood residuals. The ionic liquid can be recovered from the water phase, such as by evaporating the water and drying the ionic liquid. The recovered ionic liquid from both methods can then be reused. A flowchart describing these methods is provided in FIG. 2.

EXPERIMENTAL

The present invention will now be described with specific reference to various examples. The following examples are not intended to be limiting of the invention and are rather provided as exemplary embodiments.

Example 1

Preparation of 1-benzyl-3-methyl-imidazolium chloride

The ionic liquid was prepared with benzyl chloride (0.25 mol) and 1-methylimidazole (0.23 mol) using $CH_3CN$ as solvent in a 250 mL three-neck bottle. The mixture was refluxed for 48 hours under an argon atmosphere. After evaporation of the solvent and of the residual benzyl chloride, the pure ionic liquid was obtained. Drying of the materials took place at 120° C. under vacuum by stirring for 24 hours. The product was of a gelatinous nature at room temperature.

Example 2

Preparation of 1-methyl-3-benzyl-imidazolium dicyanamide

The ionic liquid was prepared by anion exchange reaction between 1-methyl-3-benzylimidazolium chloride (0.20 mol) and $NaN(CN)_2$ (0.21 mol) using water as the solvent. The homogenous mixture was stirred at room temperature for 12 hours. After evaporation of the water, 50 mL of $CH_2Cl_2$ was added into the residue. The formed NaCl was filtered, and the organic solvent phase was dried with anhydrous $MgSO_4$. After filtration of the $MgSO_4$ and evaporation of the solvent, a yellow liquid ionic liquid was obtained.

Example 3

Dissolution of Spruce

A solution of 8% by wt. Spruce wood thermomechanical pulp (TMP) in ionic liquid (1-butyl-3-methyl imidazolium chloride) was prepared by combining the components and mechanically stirring at 110° C. over an 8 hour time period.

Example 4

Dissolution of Pine

A solution of 5% by wt. Pine TMP was prepared in an ionic liquid formed using 1-allyl-3-methyl imidazolium chloride. The solution was prepared by combining the components and mechanically stirring at 110° C. over an 8 hour time period.

Example 5

Dissolution of Lignin

Ionic liquid (10 g) was charged into a 50 ml dried flask under inert atmosphere (Argon). The temperature of the dissolution process was controlled using an oil bath at 120° C. Dried lignin (Kraft pine, Kraft hardwood, or lignosulfonate) was added into the ionic liquid to form a 10% w/w solution prepared over two hours under mechanical stirring. The dissolution of lignin in ionic liquid results in the formation of a viscous, brown-black solution.

Example 6

Pyrolysis of Wood Dissolved in Ionic Liquid

A 10% (w/w) mixture of southern pine wood powder (particle size 60-150 mesh) and ionic liquid (1-allyl-3-methyl-imidazolium chloride) was used (2 g wood powder dissolved in 20 g ionic liquid). The resulting transparent mixture was then placed in a distillation flask which was connected to distillation apparatus as illustrated in FIG. 1. The system was connected to a vacuum pump and as the pressure reached 5 mmHg the temperature was gradually increased to 200° C. over a time of 20 minutes. The first drops of distillate in the receiving flasks were observed at a temperature of 190° C. and the distillation was continued at 190-200° C. for 20 minutes.

As a comparison, wood that was not dissolved in ionic liquid was also distilled as described above. In the wood without ionic liquid, a sample of original wood was tested, and a sample treated with chromated copper arsenate (CCA) was tested. For the wood dissolved in the ionic liquid, a sample of original wood was used, and a sample treated with $H_3PO_4$ was used. The yield of distillate fractions in the four different pyrolysis systems is provided in Table 3. The $H_3PO_4$ was provided as a catalyst aiding dehydration and pyrolysis; however, such addition is not required. Beneficially, the ionic liquid media itself has shown to provide a catalytic effect.

TABLE 3

| Pyrolysis Method | Samples | % Tar | % Distillate | % Char | Total Recovery |
|---|---|---|---|---|---|
| Wood without ionic liquid | Original wood | 54.5 | 12.5 | 27.5 | 94.4 |
| | CCA-treated wood | 52.2 | 15.2 | 30.4 | 94.5 |
| Wood in ionic liquid | Original wood | 65.0 | 22.0 | 15.0 | 100.0 |
| | $H_3PO_4$ treated original wood | 36.0 | 24.5 | 15.0 | 75.5 |

The combined yields of tar and distillate are vastly improved when the thermolysis is carried out under the homogeneous conditions provided by the ionic liquids with concomitant reduction in the amounts of the remaining char. For wood alone, these numbers amount to an increase of tar and distillates of 20% with an accompanying reduction of the char residue. It is also important to note that the thermolysis conditions created by the ionic liquid provided for greater amounts of more volatile products as evidenced by the higher percentages of distillate obtained. This can be very important since these distillates can be more readily refined and/or completely burned for fuel as pyrolysis oils.

Example 7

Figure 3:
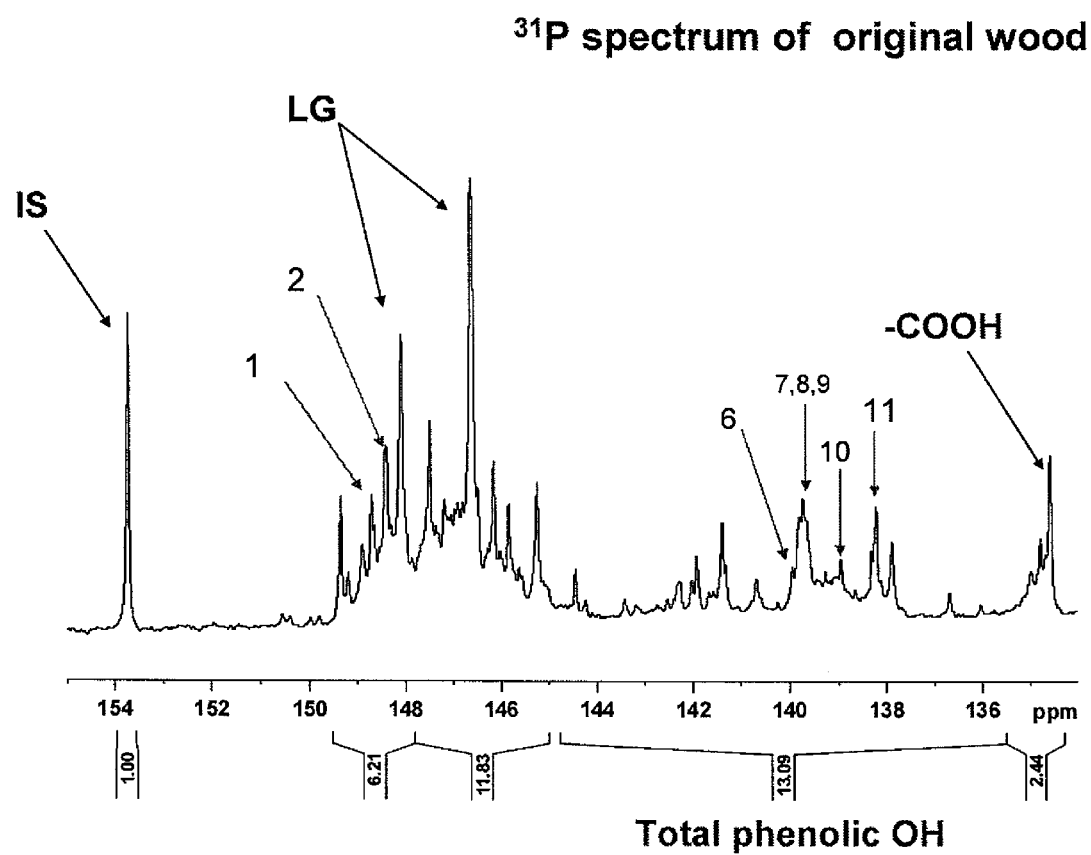
FIG. 3 is a spectral analysis of a tar fraction collected from the pyrolysis of lignocellulose dissolved in ionic liquid and distilled according to one embodiment of the invention.

Spectral Analysis of Pyrolysis Products $^{31}P$ NMR spectroscopy and gas chromatography (GC-FID) were used as parallel analytical tools for identifying the chemical compositions of the pyrolysis fractions from Example 6. Table 4 shows the distinctive $^{31}P$ NMR chemical shifts for the chemical compounds typically present in pyrolysis distillate fractions. A spectral analysis of a $^{31}P$ spectrum of a tar fraction collected in the pyrolysis is provided in FIG. 3. The known values of Table 4 allow for spectral analysis of distillate fractions obtained according to the invention. The ability to obtain such valuable chemicals from lignocellulosic materials is provided by the present invention particularly in light of the increased ability to solubilize the lignocellulosic materials through use of the ionic liquid media.

TABLE 4

| Chemical | Chemical Shift (ppm) | Chemical Shift (ppm) |
|---|---|---|
| 5-hydroxymethyl-2-furaldehyde | 148.71 | |
| Acetol | 148.43 | |
| Furfuryl alcohol | 148.32 | |
| Levoglucosan (standard) | 148.10 | 146.65 |
| Experimental Levoglucosan | 148.09 | 146.6-146.63 |
| Furfural | 147.09 | |
| 2-methoxy-4-methyl phenol | 139.96 | |
| 4-ethyl-2-methoxy phenol | 139.88 | |
| Guaiacol | 139.73 | |
| Isoeugenol | 139.73 | |
| Catechol | 138.94 | |
| p-Cresol | 138.21 | |
| Phenol | 138.01 | |
| Levoglucosenone | 135.88 | |
| Acetic acid | 134.58 | |
| Unknown | 141.32 | |

Analysis of the tar fraction indicated that the yield of levoglucosan (LG) is significantly lower in ionic liquid pyrolysis media. This is shown in Table 5. In contrast, the yield of LGO was found to increase when ionic liquid was used as the reaction medium being roughly 5 times higher if compared to the conventional system. This is shown below in Table 6. Both LG and LGO are valuable chemicals to be used as precursors in the pharmaceutical industry. In addition, LGO is a prochiral compound thus being even more valuable than LG. As LGO is a dehydration product of LG, the obtained results indicate ionic liquids have unique properties in controlling the reaction. The lower yield of LG in the final product obtained using ionic liquid media indicates that the conversion of LG to LGO has been more complete when the ionic liquid is used. This is particularly useful since LGO is a more desirable end product than it precursor, LG.

TABLE 5

| Samples | LG (%) |
| --- | --- |
| Original wood | 3.7 |
| CCA-treated wood | 18.3 |
| H$_3$PO$_4$-treated original wood | 19.95 |
| H$_3$PO$_4$-treated CCA wood | 20.53 |
| Microcrystalline cellulose | 42.5 |
| Microcrystalline cellulose, H+ | 40.5 |
| Original wood in Ionic Liquid | 0.06 |
| H$_3$PO$_4$-treated original wood in Ionic Liquid | 0.06 |

TABLE 6

| Sample | Yield of LGO (mmol/g) | Yield of LGO (%) |
| --- | --- | --- |
| Original wood | 0.0495 | 0.6 |
| CCA-treated wood | 0.0715 | 0.9 |
| H$_3$PO$_4$-treated original wood | 0.0454 | 0.6 |
| H$_3$PO$_4$-treated CCA wood | 0.0994 | 1.3 |
| Microcrystalline cellulose | 0.117 | 1.5 |
| Microcrystalline cellulose, H+ | 0.213 | 2.7 |
| Original wood in Ionic Liquid | 0.225 | 2.8 |
| H$_3$PO$_4$-treated original wood in Ionic Liquid | 0.227 | 2.9 |

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for thermolysis of a lignocellulosic material to form a recoverable product, the method comprising combining the lignocellulosic material with an ionic liquid to form a mixture wherein the lignocellulosic material is at least partially dissolved and heating the mixture such that thermolysis of the lignocellulosic material occurs and to form a fraction comprising the recoverable product.

2. The method of claim 1, comprising heating the mixture to a temperature of about 150° C. to about 300° C.

3. The method of claim 2, comprising heating the mixture anaerobically.

4. The method of claim 1, wherein the fraction comprises a distillation fraction.

5. The method of claim 1, wherein the fraction comprises a tar fraction.

6. The method of claim 1, wherein the recoverable product comprises one or more commodity chemicals.

7. The method of claim 6, wherein the one or more commodity chemicals is selected from the group consisting of levoglucosenone, levulonic acid, levulinic acid, 5-hydroxymethyl furfural, 2-furaldehyde (furfural), 2-methylfurfural, and combinations thereof.

8. The method of claim 1, wherein the ionic liquid comprises a material formed of a cation and an anion, wherein the cation is selected from the group consisting of imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, derivatives thereof, and combinations thereof, and wherein the anion is selected from the group consisting of halogens, phosphates, BF$_4^-$, PF$_6^-$, AsF$_6^-$, NO$_3^-$, N(CN)$_2^-$, N(SO$_3$CF$_3$)$_2^-$, amino acids, substituted or unsubstituted carboranes, perchlorates, pseudohalogens, metal chloride-based Lewis acids, C$_{1-6}$ carboxylates, and combinations thereof.

9. The method of claim 8, wherein the cation is selected from the group consisting of imidazoles and pyridines, and the anion is selected from the group consisting of halogens, phosphates, alkylphosphates, alkenylphosphates, and bis(trifluoromethylsulfonyl)imide.

10. The method of claim 1, wherein the lignocellulosic material is selected from the group consisting of tobacco, corn, corn stovers, corn residues, cornhusks, sugarcane bagasse, castor oil plant, rapeseed plant, soybean plant, cereal straw, grain processing by-products, bamboo, bamboo pulp, bamboo sawdust, energy grasses, rice straw, paper sludge, waste papers, recycled paper, recycled pulp, and combinations thereof.

11. The method of claim 10, wherein the lignocellulosic material is a wood.

12. The method of claim 10, wherein the lignocellulosic material, prior to combining with the ionic liquid, is in a form selected from the group consisting of ball-milled wood powder, sawdust, thermomechanical pulp fibers, wood chips, and combinations thereof.

13. The method of claim 1, wherein the mixture further comprises a catalyst.

14. The method of claim 13, wherein the catalyst comprises an acid.

15. The method of claim 1, wherein the lignocellulosic material is at least partially dissolved and undergoes thermolysis in a single step, thereby eliminating the need for performing multiple processing steps and different reactor configurations.

16. A method of preparing a commodity chemical from a lignocellulosic material, the method comprising combining the lignocellulosic material with an ionic liquid to form a mixture wherein the lignocellulosic material is at least partially dissolved, distilling the mixture, and recovering the commodity chemical; wherein the distilling step comprises heating to a temperature of about 150° C. to about 300° C.

17. The method of claim 16, wherein the commodity chemical is selected from the group consisting of alcohols, phenols, aldehydes, organic acids, furans, catechols, and combinations thereof.

18. The method of claim 17, wherein the commodity chemical is selected from the group consisting of levoglucosenone, levulonic acid, levulinic acid, 5-hydroxymethyl furfural, 2-furaldehyde (furfural), 2-methylfurfural, and combinations thereof.

19. The method of claim 18, wherein the commodity chemical comprises levulinic acid.

20. The method of claim 16, wherein the ionic liquid comprises a material formed of a cation and an anion, wherein the cation is selected from the group consisting of imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, derivatives thereof, and combinations thereof, and wherein the anion is selected from the group consisting of halogens, phosphates, $BF_4^-$, $PF_6^-$, $AsF_6^-$, $NO_3^-$, $N(CN)_2^-$, $N(SO_3CF_3)_2^-$, amino acids, substituted or unsubstituted carboranes, perchlorates, pseudohalogens, metal chloride-based Lewis acids, $C_{1-6}$ carboxylates, and combinations thereof.

21. The method of claim 20, wherein the cation is selected from the group consisting of imidazoles and pyridines, and the anion is selected from the group consisting of halogens, phosphates, alkylphosphates, alkenylphosphates, and bis(trifluoromethylsulfonyl)imide.

22. The method of claim 16, wherein the lignocellulosic material is selected from the group consisting of tobacco, corn, corn stovers, corn residues, cornhusks, sugarcane bagasse, castor oil plant, rapeseed plant, soybean plant, cereal straw, grain processing by-products, bamboo, bamboo pulp, bamboo sawdust, energy grasses, rice straw, paper sludge, waste papers, recycled paper, recycled pulp, and combinations thereof.

23. The method of claim 22, wherein the lignocellulosic material is a wood.

24. The method of claim 22, wherein the lignocellulosic material, prior to combining with the ionic liquid, is in a form selected from the group consisting of ball-milled wood powder, sawdust, thermomechanical pulp fibers, wood chips, and combinations thereof.

25. The method of claim 24, comprising heating the mixture anaerobically.

26. The method of claim 16, comprising heating the mixture in the presence of a catalyst.

27. The method of claim 26, wherein the catalyst comprises an acid.

28. A method of converting lignin to aromatic compounds, comprising:
  combining lignin with an ionic liquid to form a mixture wherein the lignin is at least partially dissolved, distilling the mixture, and recovering aromatic compounds in a distillation fraction;
  wherein the distilling step comprises heating to a temperature of about 150° C. to about 300° C.

29. The method of claim 28, wherein the aromatic compounds include levoglucosenone.

30. The method of claim 16, wherein the lignocellulosic material is at least partially dissolved and undergoes thermolysis in a single step, thereby eliminating the need for performing multiple processing steps and different reactor configurations.

* * * * *

UNITED STATES PATENT AND TRADEMARK OFFICE
CERTIFICATE OF CORRECTION

| | |
|---|---|
| PATENT NO. | : 7,959,765 B2 |
| APPLICATION NO. | : 12/026993 |
| DATED | : June 14, 2011 |
| INVENTOR(S) | : Argyropoulos |

It is certified that error appears in the above-identified patent and that said Letters Patent is hereby corrected as shown below:

Column 16,

Line 60, "salvation" should read --solvation--.

Signed and Sealed this
Twelfth Day of June, 2012

David J. Kappos
*Director of the United States Patent and Trademark Office*